United States Patent
Pham et al.

(10) Patent No.: US 7,459,130 B2
(45) Date of Patent: *Dec. 2, 2008

(54) MULTI-WELL PLATFORMS, CADDIES, LIDS AND COMBINATIONS THEREOF

(75) Inventors: Andrew A. Pham, Del Mar, CA (US); Peter J. Coassin, Encinitas, CA (US); Alec Tate Harootunian, Del Mar, CA (US); Peter N. Pham, San Diego, CA (US); Harry Stylli, San Diego, CA (US); Roger Y. Tsien, La Jolla, CA (US)

(73) Assignee: Aurora Discovery, Inc., San Diego, CA (US)

( * ) Notice: Subject to any disclaimer, the term of this patent is extended or adjusted under 35 U.S.C. 154(b) by 433 days.

This patent is subject to a terminal disclaimer.

(21) Appl. No.: 11/067,322

(22) Filed: Feb. 25, 2005

(65) Prior Publication Data

US 2005/0214174 A1    Sep. 29, 2005

Related U.S. Application Data

(63) Continuation of application No. 10/209,315, filed on Jul. 30, 2002, now Pat. No. 6,861,035, which is a continuation of application No. 09/111,553, filed on Jul. 7, 1998, now Pat. No. 6,426,050.

(51) Int. Cl.
*B01L 3/00* (2006.01)
(52) U.S. Cl. .................. 422/102; 422/104; 435/288.3; 435/288.4

(58) Field of Classification Search ............... 422/102, 422/104; 435/287.1, 288.3, 288.4
See application file for complete search history.

(56) References Cited

U.S. PATENT DOCUMENTS

| | | |
|---|---|---|
| 4,004,150 A | 1/1977 | Natelson |
| 4,154,795 A | 5/1979 | Thorne |
| 4,251,159 A | 2/1981 | White |
| 4,276,259 A | 6/1981 | Eibl et al. |
| D265,124 S | 6/1982 | Terk |

(Continued)

FOREIGN PATENT DOCUMENTS

EP    0 542 422 A1    10/1992

(Continued)

OTHER PUBLICATIONS

Corning Costar, "The 96 Well Assay Block" (1997).

(Continued)

*Primary Examiner*—Jill Warden
*Assistant Examiner*—Dwayne K Handy
(74) *Attorney, Agent, or Firm*—DLA Piper LLP (US)

(57) ABSTRACT

The present invention relates to multi-well platforms, lids, caddies and any combination thereof. The multi-well platforms comprise a plurality of wells that can be of any shape and can be arranged in any ornamental pattern. The lid comprises an area corresponding to the well field. The caddy has a footprint approximately that of a standard 96-well microtiter plate. When the multi-well platform is engaged with the caddy, the wells of the well-field of the multi-well platform are preferably not obscured by the caddy when viewed from the bottom of the combination.

20 Claims, 73 Drawing Sheets

U.S. PATENT DOCUMENTS

Figure 1:
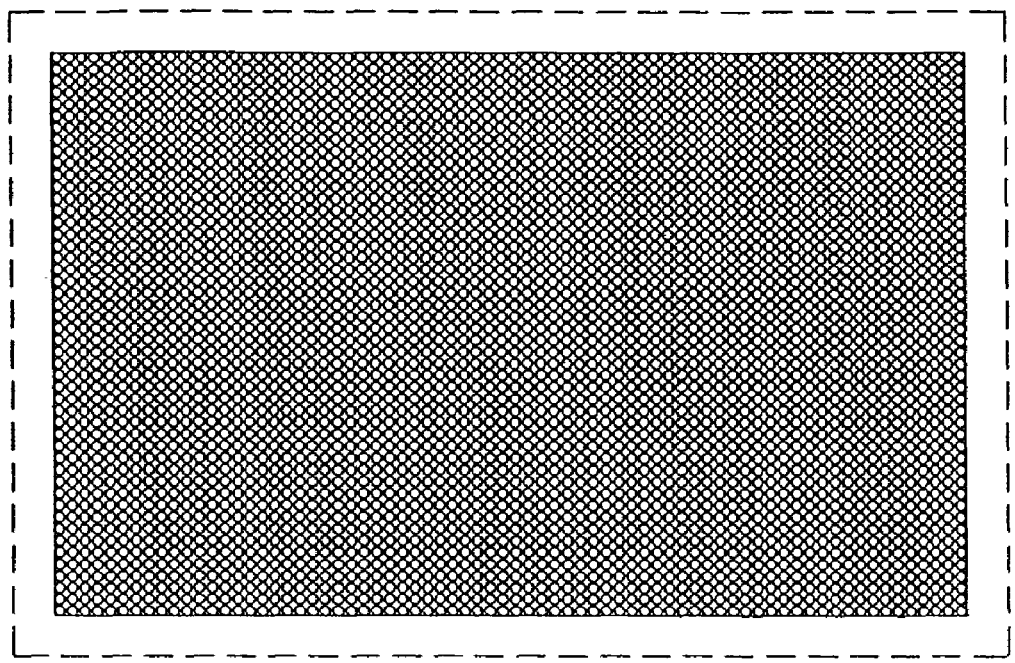

| | | | |
|---|---|---|---|
| D266,589 S | 10/1982 | Gilford et al. | |
| D269,702 S | 7/1983 | Suovaniemi et al. | |
| 4,431,307 A | 2/1984 | Suovaniemi | |
| 4,468,974 A | 9/1984 | Malinoff | |
| 4,545,958 A * | 10/1985 | Dopatka | 422/102 |
| 4,626,684 A | 12/1986 | Landa | |
| D288,604 S | 3/1987 | Winston et al. | |
| 4,652,553 A | 3/1987 | Hagmann et al. | |
| 4,657,867 A | 4/1987 | Guhl et al. | |
| 4,689,380 A | 8/1987 | Nahm | |
| 4,735,778 A * | 4/1988 | Maruyama et al. | 422/102 |
| 4,741,619 A | 5/1988 | Humphries et al. | |
| 4,770,856 A | 9/1988 | Uthemann et al. | |
| 4,797,259 A | 1/1989 | Matkovich et al. | |
| 4,828,386 A | 5/1989 | Matkovich et al. | |
| 4,874,808 A | 10/1989 | Minami et al. | |
| 4,892,409 A | 1/1990 | Smith | |
| 4,899,005 A | 2/1990 | Lane et al. | |
| 4,918,133 A | 4/1990 | Moriya et al. | |
| 4,935,475 A | 6/1990 | Kishimura et al. | |
| 4,948,442 A | 8/1990 | Manns | |
| 4,948,856 A | 8/1990 | Minchak et al. | |
| 4,956,150 A | 9/1990 | Henry | |
| 4,968,625 A | 11/1990 | Smith et al. | |
| 4,994,354 A | 2/1991 | Toibana et al. | |
| D317,360 S | 6/1991 | Gabrige | |
| 5,041,266 A | 8/1991 | Fox | |
| 5,047,215 A | 9/1991 | Manns | |
| 5,084,246 A * | 1/1992 | Lyman et al. | 422/101 |
| 5,110,556 A | 5/1992 | Lyman et al. | |
| 5,115,052 A | 5/1992 | Wamura et al. | |
| 5,147,780 A | 9/1992 | Pouletty et al. | |
| 5,149,654 A | 9/1992 | Gross et al. | |
| 5,206,306 A | 4/1993 | Shen | |
| 5,241,012 A | 8/1993 | Clark | |
| 5,270,393 A | 12/1993 | Sagane et al. | |
| 5,319,436 A * | 6/1994 | Manns et al. | 356/246 |
| 5,395,869 A | 3/1995 | Kawamoto et al. | |
| 5,428,098 A | 6/1995 | Brekner et al. | |
| 5,456,360 A | 10/1995 | Griffin | |
| 5,470,757 A | 11/1995 | Gagnon et al. | |
| 5,487,872 A * | 1/1996 | Hafeman et al. | 422/102 |
| 5,496,502 A | 3/1996 | Thomson | |
| 5,516,490 A | 5/1996 | Sanadi | |
| 5,532,030 A | 7/1996 | Hirose et al. | |
| 5,534,606 A | 7/1996 | Bennett et al. | |
| 5,540,891 A | 7/1996 | Portmann et al. | |
| 5,545,528 A | 8/1996 | Mitsuhashi et al. | |
| 5,583,211 A | 12/1996 | Coassin et al. | |
| 5,604,130 A | 2/1997 | Warner et al. | |
| 5,609,826 A | 3/1997 | Cargill et al. | |
| 5,616,461 A | 4/1997 | Schaffer et al. | |
| 5,670,113 A | 9/1997 | Akong et al. | |
| 5,728,541 A | 3/1998 | Kornblith | |
| 5,736,400 A | 4/1998 | Moses et al. | |
| 5,738,825 A * | 4/1998 | Rudigier et al. | 422/82.11 |
| 5,770,860 A | 6/1998 | Franzen | |
| 5,789,251 A * | 8/1998 | Astle | 436/48 |
| 5,792,426 A * | 8/1998 | Portmann et al. | 422/102 |
| 5,858,309 A * | 1/1999 | Mathus et al. | 422/102 |
| 5,876,946 A | 3/1999 | Burbaum et al. | |
| 5,910,287 A | 6/1999 | Cassin et al. | |
| 6,020,444 A * | 2/2000 | Riedel et al. | 526/170 |
| 6,027,695 A * | 2/2000 | Oldenburg et al. | 422/102 |
| 6,063,338 A * | 5/2000 | Pham et al. | 422/61 |
| 6,074,614 A * | 6/2000 | Hafeman et al. | 422/102 |
| 6,083,761 A * | 7/2000 | Kedar et al. | 436/178 |
| 6,232,114 B1 * | 5/2001 | Coassin et al. | 435/288.4 |
| 6,254,833 B1 * | 7/2001 | Shumate et al. | 422/102 |
| 6,258,326 B1 * | 7/2001 | Modlin | 422/102 |
| 6,426,050 B1 * | 7/2002 | Pham et al. | 422/104 |

FOREIGN PATENT DOCUMENTS

| | | |
|---|---|---|
| JP | 08040914 | 2/1996 |
| WO | WO86/07606 | 12/1986 |
| WO | WO92/01513 | 2/1992 |
| WO | WO92/01553 | 2/1992 |
| WO | WO94/23839 | 10/1994 |
| WO | WO95/22406 | 8/1995 |
| WO | WO96/39481 | 12/1996 |
| WO | WO97/05492 | 2/1997 |

OTHER PUBLICATIONS

Corning Costar, "384 Well Plates" (1997).
Millipore 1997 Laboratory Catalogue, pp. 34-40 (1997).
T. Astle, "Standards in Robotics and Instrumentation," *Journal of Biological Screening*, 1(4):163-168 (1996).
Corning Costar 1996/1997 Catalog (1996).
Corning Costar, "245 mm Square BioAssay Dish" (1996).
Corning Costar, "Assay Products for High Throughput Screening" (1996).
Corning Costar, "PCR Vessels For Peak Performance Guaranteed" (1996).
Corning Costar, "The 96 Well UV-Plate" (1996).
Hoechst Technical Information, "Topas, Cycloolefin Copolymers" (1996).
Nunc Products 1996 Catalogue (1996).
VWR Scientific Products Catalogue, pp. 1879-1894 (1996).
Corning Costar 1995 Product Selection Guide, Laboratory Products (1995).
Nunc, "FluoroNunc Samples" (1993).
Corning Costar, "384 Well Plates Turn Down the Volume Turn Up the Productivity".

* cited by examiner

MULTI-WELL PLATFORMS, CADDIES, LIDS AND COMBINATIONS THEREOF

BACKGROUND, SUMMARY AND DESCRIPTION

This application is a continuation application of U.S. application Ser. No. 10/209,315 filed Jul. 30, 2002, now issued as U.S. Pat. No. 6,861,035; which is a continuation application of U.S. application Ser. No. 09/111,553 filed Jul. 7, 1998, now issued as U.S. Pat. No. 6,426,050; which is a continuation-in-part application of U.S. application Ser. No. 09/030,578 filed Feb. 24, 1998, now issued as U.S. Pat. No. 6,171,780. The disclosure of each of the prior applications is considered part of and is incorporated by reference in the disclosure of this application.

The present invention relates to multi-well platforms, lids, caddies and any combination thereof that are generally described in U.S. patent application Ser. No. 09/111,553, filed Jul. 7, 1998 (the '553 application); U.S. patent application Ser. No. 09/030,578, filed Feb. 24, 1998 (the '578 application), U.S. patent application Ser. No. 09/028,283, filed Feb. 24, 1998 (the '283 application), U.S. patent application Ser. No. 08/858,016, filed May 16, 1997 (the '016 application), U.S. patent application Ser. No. 08/867,567, filed Jun. 2, 1997 (the '567 application), U.S. patent application Ser. No. 08/868,018, filed Jun. 3, 1997 (the '018 application), U.S. patent application Ser. No. 08/867,584, filed Jun. 2, 1997 (the '584 application), and U.S. patent application Ser. No. 08/868,049, filed Jun. 3, 1997 (the '049 application); each of which is incorporated herein by reference. Designs for the multi-well platforms, lids, and caddies of the present invention have been set forth in the '578 application, the '283 application, the '567 application, the '018 application, the '584 application, and the '049 application. Designs for the multi-well platform have also been described in U.S. patent application Ser. No. 29/081,749, filed Jan. 7, 1998 (the '749 application), U.S. patent application Ser. No. 29/081,969, filed Jan. 12, 1998 (the '969 application) and U.S. patent application Ser. No. 29/081,976, filed Jan. 12, 1998 (the '976 application), each of which is incorporated herein by reference. The multi well platforms, lids, caddies and combinations described herein can be used in any of the methods or other aspects of the inventions described in the '578 application, the '283 application, the '016 application, the '567 application, the '018 application, the '584 application, or the '049 application.

Multi-Well Platforms

The multi-well platforms of the present invention are well suited for use in fluorescent based assays, but can be used for any appropriate purpose. These multi-well platforms comprise a frame, wherein said wells are disposed in said frame. The frame can be of any thickness, such as between about 0.5, 1, 2, 3, or 5 millimeters and 2, 3, 5, 10 or 20 millimeters. The frame can be made of any material, such as polymers, such as polystyrene or cycloolefins, or other materials, such as glass or quartz. The frame can be of any shape, and typically defines the footprint of the multi-well platform.

The bottom of the frame can be substantially flat, meaning in this instance that the bottom of the frame does not have additional structures, such as means to form a band of opaque material in the bottom when the frame and bottom are sealed together (see, U.S. Pat. No. 5,319,436 (Mann et al.)). Such bands of opaque material are preferred when the wall is chamfered, however, the present invention is useful with or without such bands of opaque material. The bottom of the frame can also include structures such as pins, grooves, flanges or other known structures or those developed in the future to orient the multi-well platform on another structure, such as a detector or another platform.

The multi-well platform can have a footprint of any shape or size, such as square, rectangular, circular, oblong, triangular, kidney, or other geometric or non-geometric shape. The footprint can have a shape that is substantially similar to the footprint of existing multi-well platforms, such as the standard 96-well microtiter plate, whose footprint is approximately 85.5 mm in width by 127.75 mm in length or other sizes that represent a current or future industry standard (see T. Astle, Standards in Robotics and Instrumentation, J. of Biomolecular Screening, Vol. 1 pages 163-168 (1996)). Multi-well platforms of the present invention having this footprint can be compatible with robotics and instrumentation, such as multi-well platform translocators and readers as they are known in the art.

Each well comprises a wall having less fluorescence than polystyrene wall of 100 to 70% of the wall's thickness, preferably at least 90 percent of the wall's thickness. These determinations can be made using fluorescent detection methods well known in the art, such as determining the fluorescence of appropriate sheets of the materials being compared or as described herein.

Typically, wells will be arranged in two-dimensional linear arrays on the multi-well platform. However, the wells can be provided in any type of array, such as geometric or non-geometric arrays. The number of wells can be no more than 864 wells, or greater than 864 wells, on a standard multi-well platform footprint. Larger numbers of wells or increased well density can also be easily accomplished using the methods of the claimed invention. Other commonly used number of wells include 1536, 3456, and 9600. The number of wells can be between about 50, 100, 200, 500, 700, 800 or 1000 wells and 150, 250, 600, 800, 1000, 2000, 4000 5000, or 10000 wells. Preferably, the number of wells can be between about 50 and 10000, more preferable between about 800 and 5000, and most preferably between about 900 and 4000. The number of wells can be a multiple of 96 within these ranges, preferably the square of an integer multiplied by 96.

Well volumes typically can vary depending on well depth and cross sectional area. Well volumes can range between about 0.5, 1, 5, 10, 25, 50, 75, 100 or 200 microliter and about 5, 15, 40, 80, 100, 200, 500, or 1000 microliters. Preferably, the well volume is between about 500 nanoliters and 500 microliters, more preferably between about 1 microliter and 200 microliter, and most preferably between about 0.5 microliters and 10 microliters.

Wells can be made in any cross sectional shape (in plan view) including, square, round, hexagonal, other geometric or non-geometric shapes, and combinations (intra-well and inter-well) thereof. Wells can be made in any cross sectional shape (in vertical view) including shear vertical or chamfered walls, wells with flat or round bottoms, conical walls with flat or round bottoms, and curved vertical walls with flat or round bottoms, and combinations thereof.

Figure 135A:
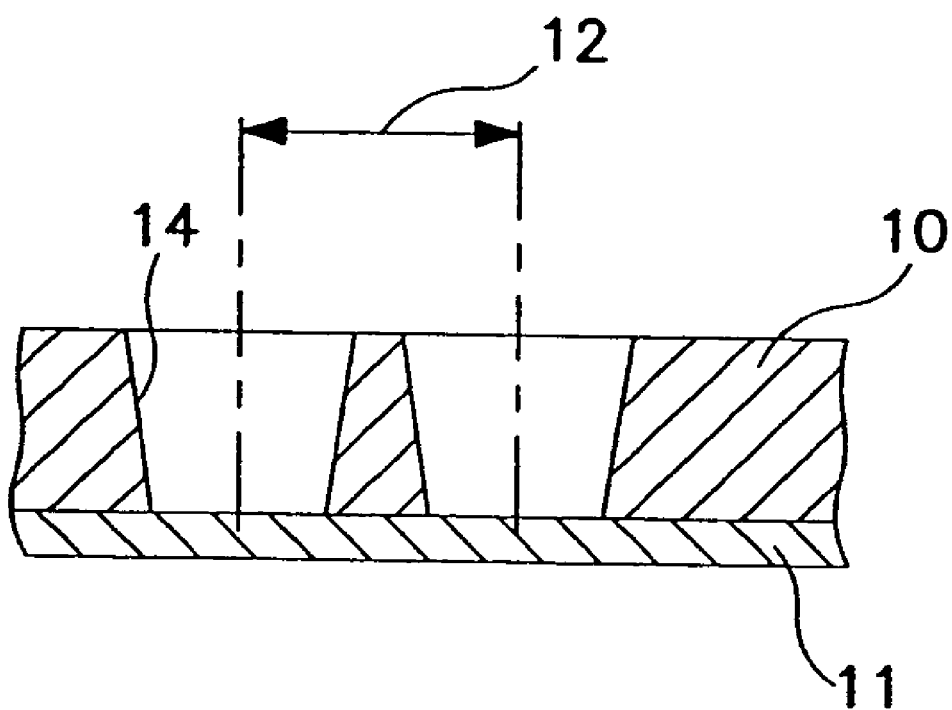

As shown in FIG. 135A, the walls can be chamfered (e.g. having a draft angle) 14. Chamfered walls can have an angle between about 1, 2, 3, 4, or 5 degrees and about 2, 3, 4, 5, 6, 7, 8, 10, or 20 degrees. Preferably, the angle is between about 1 and 10 degrees, more preferably between about 2 and 8 degrees, and most preferable between about 3 and 5 degrees.

As shown in FIG. 135, the wells can be placed in a configuration so that the well center-to well-center distance 12 can be between about 0.5, 1, 2, 5, or 10 millimeters and about 1, 2, 5, 10, 20, 50, or 100 millimeters. The wells can be placed in any configuration, such as a linear-linear array, or geometric patterns, such as hexoginal patterns. The well-to-well distance can be about 9 mm divided by an integer between 1 and 10. Typically, the multi-well plate has wells with a well-center-to-well-center distance of less than about 2.5 mm, preferably less than 2 mm and some times less than about 1 mm. Smaller well-center to well-center distances are preferred for smaller volumes.

The wells can have a depth between about 0.5, 1, 2, 3, 4, 5, 10, 20, or 50 millimeters and about 5, 10, 20, 50, or 100 millimeters. Preferably, the well depth is between about 1 millimeter and 100 millimeters, more preferably between about 2 millimeters and 50 millimeters, and most preferably between about 3 millimeters and 20 millimeters.

The wells can have a diameter (when the wells are circular) or maximal diagonal distance (when the wells are not circular) between about 0.2, 0.5, 0.7, 1, 5, 10, or 50 millimeters and about 1, 5, 10, 20, 50, or 100 millimeters. Preferably, the well diameter is between about 0.5 and 100 millimeters, more preferably between about 1 and 50 millimeters, and most preferably, between about 2 and 20 millimeters.

The wells of the multi-well platform can comprise an optically opaque material that can interfere with the transmission of radiation, such as light, through the wall of a well or bottom of a well. Such optically opaque materials can reduce the background associated with optical detection methods. Optically opaque materials can be any known in the art or later developed, such as dyes, pigments or carbon black. The frame can be made of an optically opaque material, or the walls or bottom, or both, can be coated with an optically opaque material. The optically opaque material can prevent radiation from passing from one well to another, to prevent cross-talk between wells, so that the sensitivity and accuracy of the assay is increased. The optically opaque material can also be reflective, such as those known in the art, such as thin metal layers, mirror coatings, or mirror polish. Optically opaque materials can be coated onto any surface of the multi-well platform, or be an integral part of the frame or bottom as they are manufactured. Optically opaque material can prevent the transmittance of between about 100% to about 50% of incident light, preferably between about 80% and greater than 95%, more preferably greater than 99%.

Since most measurements will not typically require light to pass through the wall of the well, materials such as polymers can include pigments to darken well walls or absorb light. Such application of pigments will help reduce background fluorescence. Pigments can be introduced by any means known in the art, such as coating or mixing during the manufacture of the material or multi-well platform. Pigment selection can be based on a mixture of pigments to dampen all background inherent to the polymer, or a single pigment or ensemble of pigments selected to filter or absorb light at desired wavelengths. Pigments can include carbon black. Such pigmentation is generally not desired in embodiments where light is directed through the well wall as a method for illuminating the contents of the well.

Each well also comprises a bottom 11 having a high transmittance portion and having less fluorescence than a polystyrene-bottom of at least about 90 percent of said bottom's thickness. This property can be determined by comparing the fluorescence of an appropriate control bottom material with the fluorescence of a test material. These procedures can be performed using well known methods. The thickness of the bottom can vary depending on the overall properties required of the plate bottom that may be dictated by a particular application. Preferably, the bottom is a plate or film as these terms are known in the art. Such properties include the amount of intrinsic fluorescence, rigidity, breaking strength, and manufacturing requirements relating to the material used in the plate. Well bottom layers typically have a thickness between about 10, 15, 20, 50, 100, 200, or 300 micrometers and about 20, 50, 100, 200, 300, 450, 500, or 1000 micrometers. Preferably, the well bottom has a thickness between about 10 micrometers and 450 micrometers, more preferably between about 15 micrometers and 300 micrometers, and most preferably between about 20 micrometers and 100 micrometers.

Figure 135B:
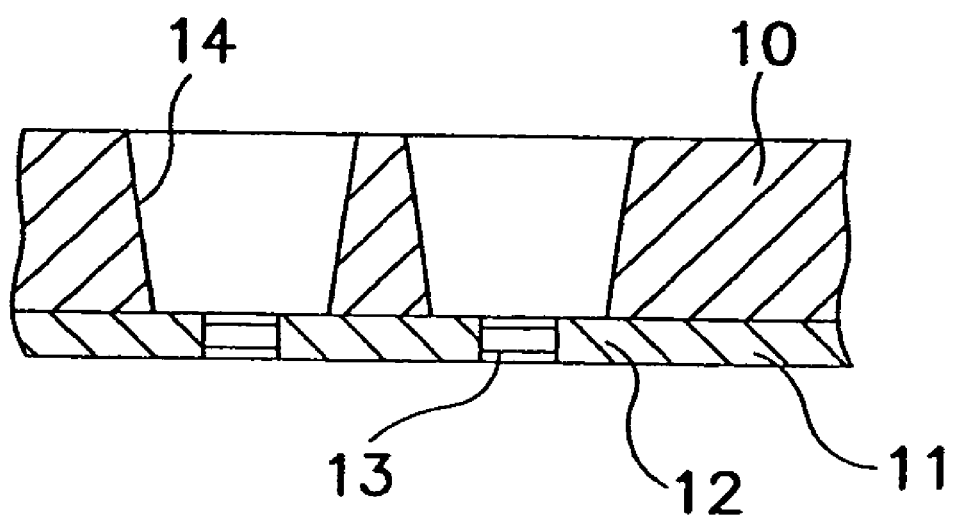

The bottom of a well can have a high transmittance portion, typically meaning that either all or a portion of the bottom of a well can transmit light. As shown in FIG. 135B, the bottom can have an optically opaque portion 12 and a high transmittance portion 13 of any shape, such as circular, square, rectangular, kidney shaped, or other geometric or non-geometric shape or combinations thereof. In applications of the invention that can utilize focused light, the bottom, or a portion thereof, can be used to form a lens. Lens will vary in thickness and curvature depending on the application, such as convex or concave in shape.

The bottom can produce about 200 percent or less of the fluorescence compared to glass of 100 microns thickness at excitation wavelengths between about 290, 300, 310, 320, or 350 to about 300, 340, 370, 400, or 420 nm and at emission wavelengths between about 290, 300, 350, 400, or 500 and about 400, 600, 800, or 1000 nm.

Preferably, the bottom of the multi-well platform can be substantially flat, e.g. having a surface texture between about 0.001 mm and 2 mm, preferably between about 0.01 mm and 0.1 mm (see, Surface Roughness, Waviness, and Lay, Am. Soc. of Mech. Eng. #ANSI ASME B46.1-2985 (1986)). If the bottom is not substantially flat, then the optical quality of the bottom and wells can decrease because of altered optical and physical properties of one or both. Furthermore, the bottom of the frame can be substantially flat within the meaning set forth in this paragraph.

One feature of the preferred multi-well platform of the present invention is their low intrinsic fluorescence. Bottom layers comprising cycloolefin typically produces about 100 to 200 percent or less of the fluorescence compared to glass of about 130 to 170 micrometers in thickness. Glass, particularly fused silica, is typically used a "gold standard" for comparison of relative fluorescence. Fluorescence and relative fluorescence can be measured using any reliable techniques known or developed in the art, preferably the techniques described herein are used. Preferably, the glass standard used herein to show the surprisingly low fluorescence of polymers such as cycloolefin is used as a standard. Preferably, the bottom typically produces about 100 to 200 percent or less of the fluorescence compared to glass of about 0.085 to 0.13 millimeters (85 to 130 micrometers) thick (for glass slides, see Thomas Scientific, MicroCover Glasses, No. 0, product No. 6661-B40). The amount of intrinsic fluorescence can be dictated, in part, by the layer thickness. In some applications that can tolerate particularly thin bottoms, such as applications where the bottom does not require significant structural strength, layer thickness can be quite thin (e.g., 20 to 80 microns) in order to reduce fluorescence arising from the bottom. The thinness of a bottom is usually also balanced against the difficulty of uniformly welding or generating thinner layers in manufacturing processes. The low relative fluorescence of the multi-well platform is usually present at excitation wavelengths between about 300 to 400 nm and at emission wavelengths between about 350 to 800 nm.

The bottom or wells can also include at least one or a plurality of living cells. The cells can be prokaryotic, such as bacteria, or eukaryotic, such as plant cells, mammalian cells, or yeast cells. The cells can include more than one type of cell, such as a mixture of different mammalian cells, or a mixture of prokaryotic and eukaryotic cells. Such embodiments are useful for cell based assays described herein and for growing cells using culture methods. The multi-well platforms of the invention can include a coating (e.g., polylysine or fibronectin) to enhance attachment of cells. Coatings can also include at least one substrate for a cell adhesion molecule, such as integrins. Such substrates are known in the art.

The multi-well platform of the present invention can include coatings or surface modifications to facilitate various applications of the plate as described herein and known or developed in the relevant art. Coatings can be introduced using any suitable method known in the art, including printing, spraying, radiant energy, ionization techniques or dipping. Surface modifications can also be introduced by appropriately derivatizing a polymer or other material, such as glass or quartz, before, during, or after the multi-well platform is manufactured and by including an appropriate derivatized polymer or other material in the bottom layer or frame. The derivatized polymer or other material can then be reacted with a chemical moiety that is used in an application of the plate. Prior to reaction with a chemical moiety, such polymer or other material can then provide either covalent or non-covalent attachment sites on the polymer or other material. Such sites in or on the polymer or other material surface can be used to attach moieties, such as assay components (e.g., one member of a binding pair), chemical reaction components (e.g., solid synthesis components for amino acid or nucleic acid synthesis), and cell culture components (e.g., proteins that facilitate growth or adhesion). Examples of derivatized polymers or other materials include those described by U.S. Pat. No. 5,583,211 (Coassin et al.) and others known in the art or later developed. Particularly preferred embodiments are based on polyethylene and polypropylene derivatives that can be included as cycloolefin copolymers.

The materials for manufacturing the multi-well platform will typically be polymeric, since these materials lend themselves to mass manufacturing techniques. However, other materials can be used to make the frame or bottom of the multi-well platform, such as glass or quartz. The frame and bottom can be made of the same or different materials and the bottom can comprise polystyrene, or another material. Preferably, polymers are selected that have low fluorescence or other properties using the methods described herein. The methods herein can be used to confirm that selected polymers possess the desire properties. Polymeric materials can particularly facilitate plate manufacture by molding methods known in the art and developed in the future, such as insert or injection molding.

Figure 7:
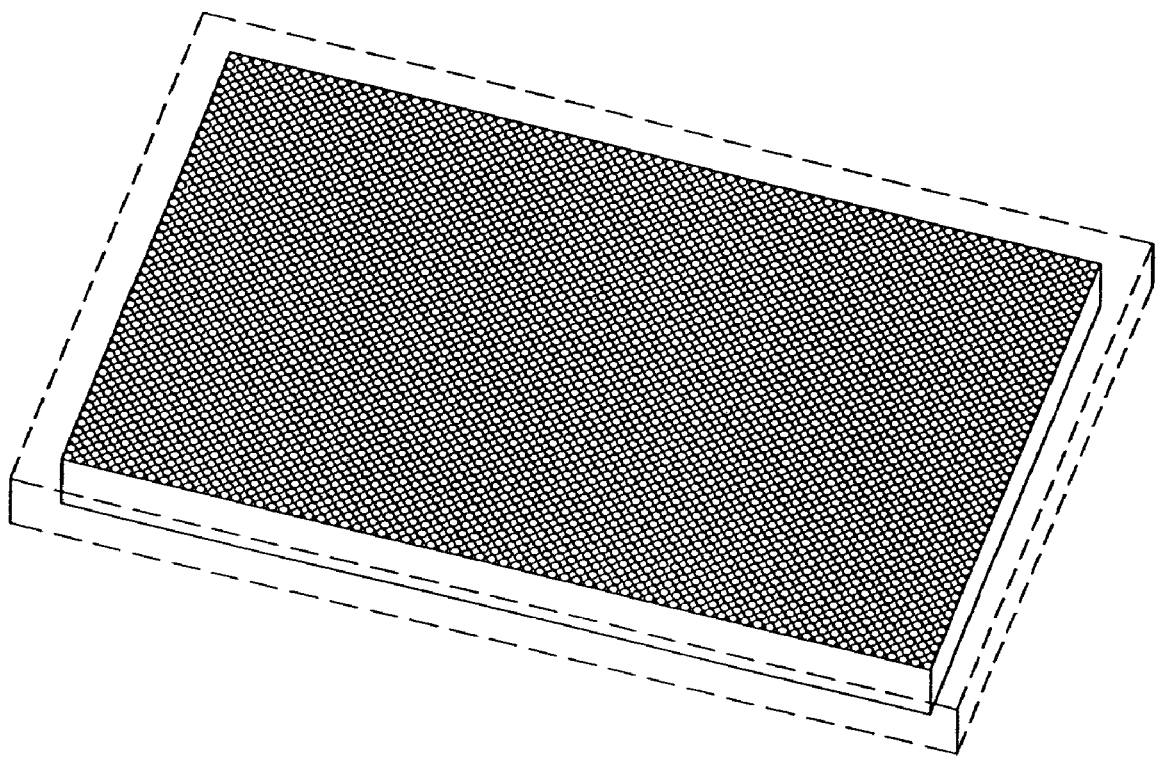

Generally, the multi-well platforms of the present invention comprise two regions, a well field and a border. The well field can have any structure (or lack of structure), preferably having any number of wells, more preferably about 3,456 wells (see, FIG. 7). The wells can be of any shape and can be arranged in any ornamental pattern, including patterns such as hexagonal arrays. In FIG. 7, the material forming the well field is pigmented, but such pigmentation is optional.

Figure 14:
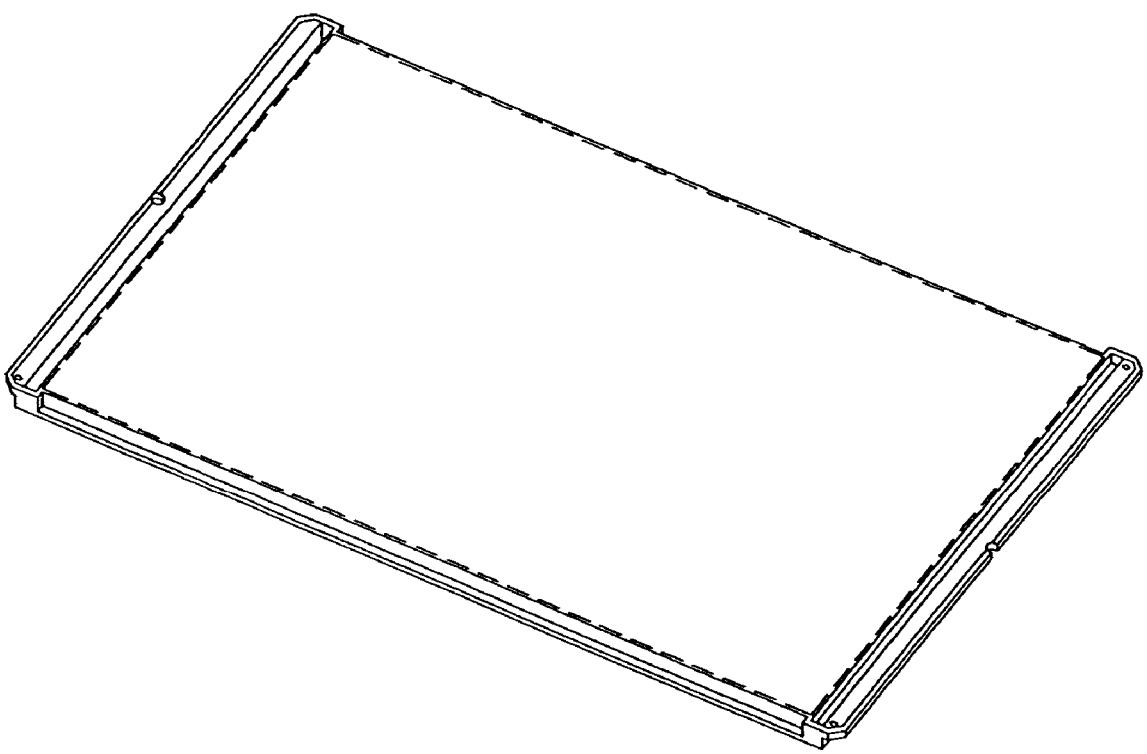
Figure 21:
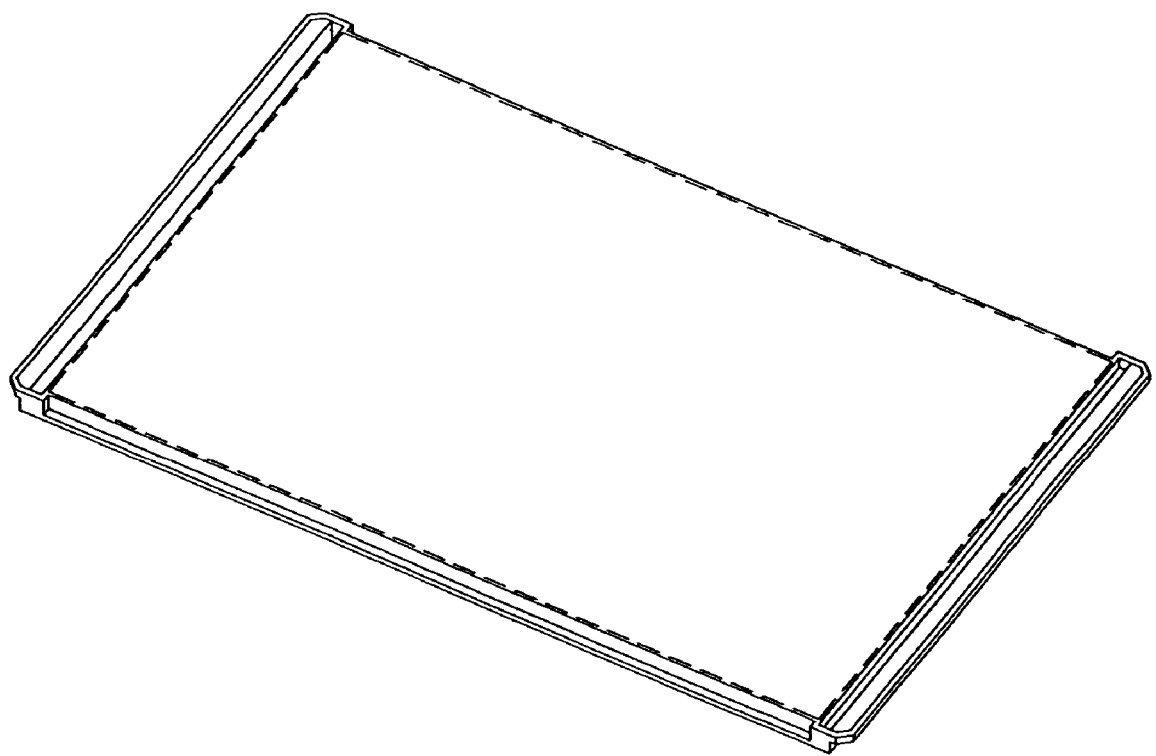

The border can be any dimension, shape, or thickness, but preferably forms a multi-well platform with outer dimensions that are similar to those of a standard 96-well microtiter plate. As shown in FIG. 14 and FIG. 21, the border can optionally have a variety of structures, including for example, flanges, grooves, indentations, holes, and the like that add additional ornamentation to the multi-well platform. These structures can be provided either alone or in combination anywhere on the border.

Figure 49:
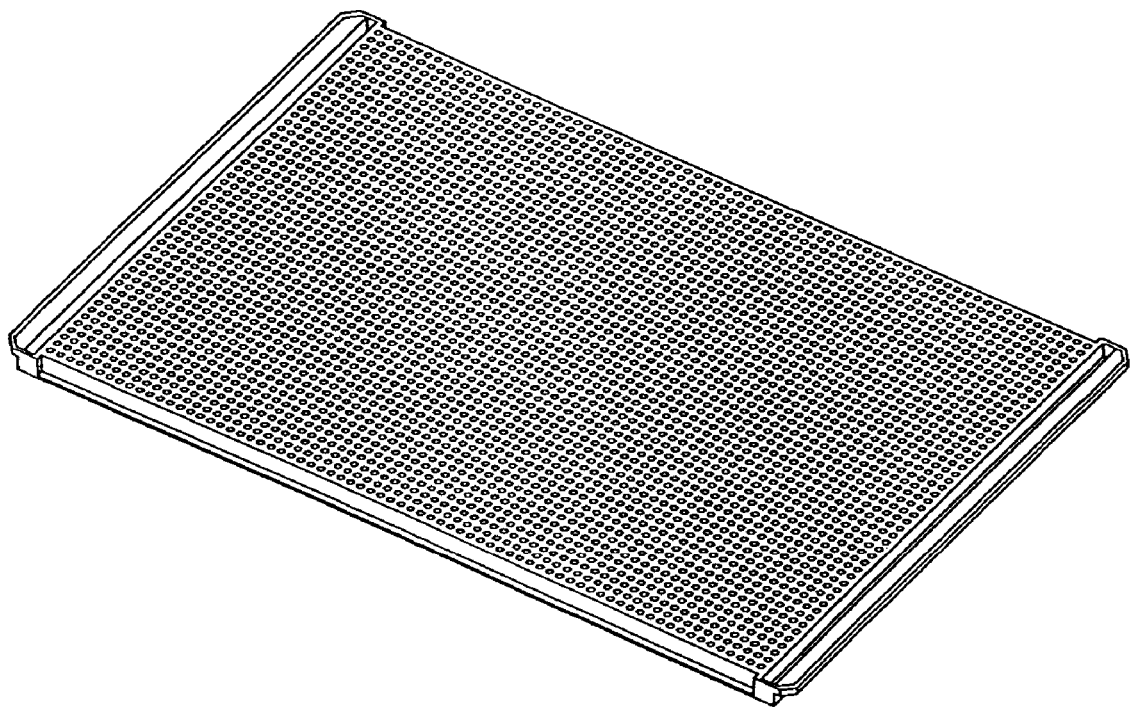
Figure 56:
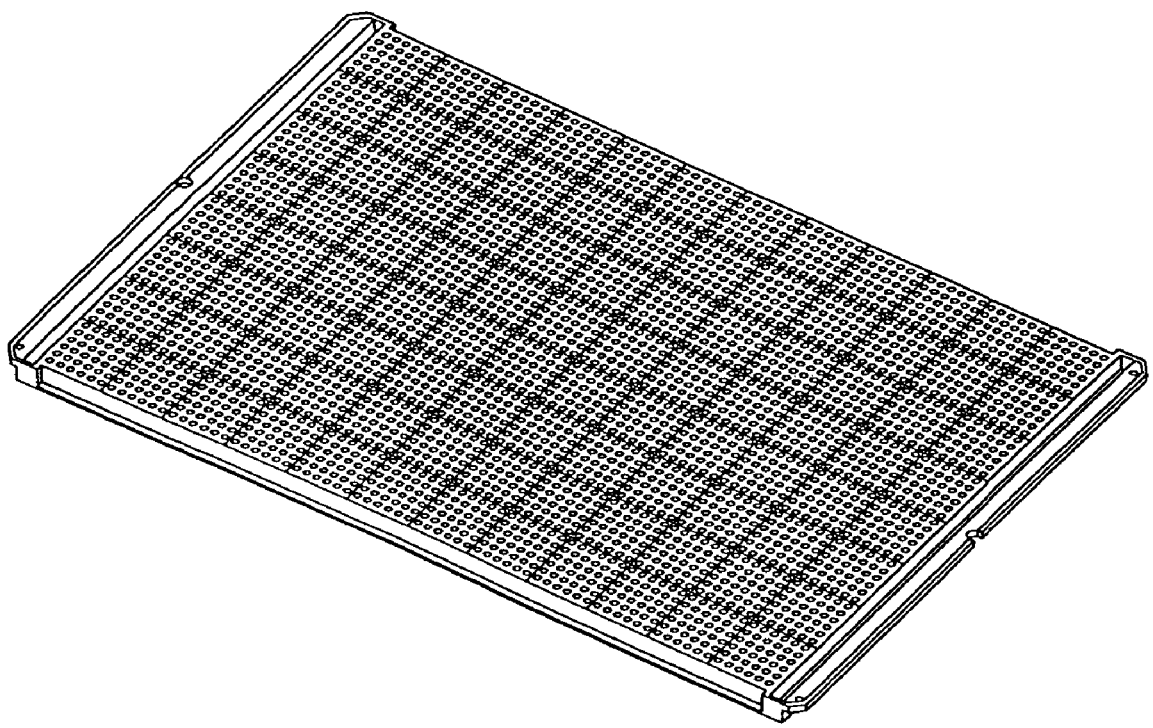

Preferred multi-well platforms are set forth in FIG. 49 and FIG. 56, which have 3,456 wells in an ornamental pattern with an ornamental border forming a footprint approximately that of a standard 96-well microtiter plate. As shown in FIG. 56, the surface of the well field can have additional ornamentation.

The multi-well platform of the present invention can optionally be fitted with an ornamental lid. The lid comprises an area corresponding to the well field and a border (see, FIG. 63). The area corresponding to the well field can be any structure (or lack thereof) that is preferably substantially flat (see, FIG. 77) but can have any non-flat configuration. The area corresponding to the well field can optionally have additional ornamentation (see, FIG. 79 and FIG. 85). The border can have a variety of ornamental excerpts (see, FIG. 63) and can optionally include additional ornamentation on any surface (see, FIG. 77, FIG. 84 and FIG. 100).

Figure 107:
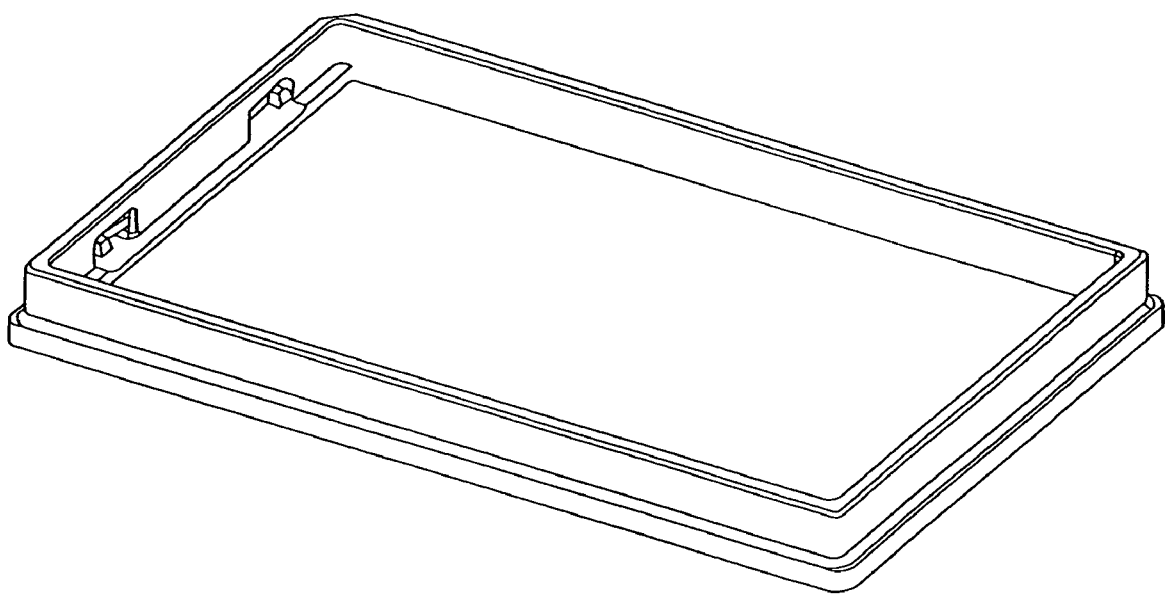

The multi-well platform of the present invention can optionally be fitted with an ornamental caddy (see, FIG. 107). The caddy has a footprint approximately that of a standard 96-well microtiter plate. When the multi-well platform is engaged with the caddy, the wells of the well-field of the multi-well platform are preferably not obscured by the caddy when viewed from the bottom of the combination (see, FIG. 120). The caddy can optionally have additional ornamentation on at least one of its four sides (see, FIG. 103). Additional ornamentation, such as for example, pins, grooves, flanges, indentations, can be optionally present on any surface of the caddy (see, FIG. 101, FIG. 109, FIG. 110, FIG. 116, FIG. 117 and FIG. 118). These types of ornamentation can be placed anywhere on the caddy, either alone or in any combination.

Any multi-well platform of the present invention can be engaged with any caddy of the present invention (see, FIG. 126) to form an ornamental combination. Furthermore, any multi-well platform of the present invention can be engaged with any caddy of the present invention and any lid of the present invention to form an ornamental combination (see, FIG. 134).

Other aspects of the present invention are provided in the figures, all of which are drawn approximately to scale. Generally, any multi-well platform, caddy, lid or combination thereof can have any feature or combination of features described herein.

DRAWINGS AND BRIEF DESCRIPTION OF THE DRAWINGS

The following provides drawings and descriptions of the multi well platforms, lids, caddies and combinations of the present invention.

A. Multi Well Platform

Figure 2:
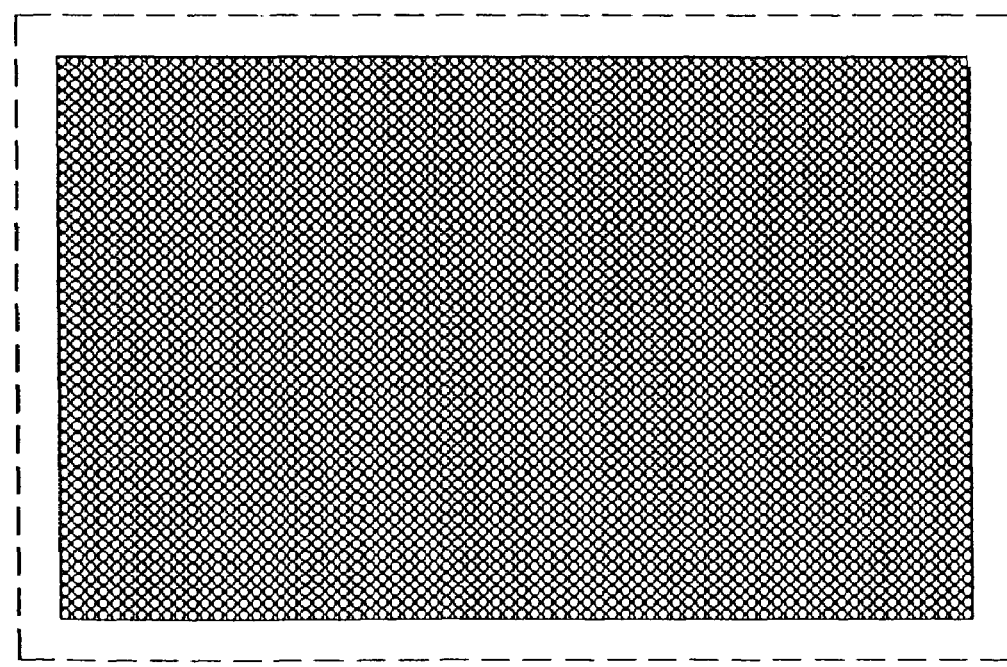
Figure 3:
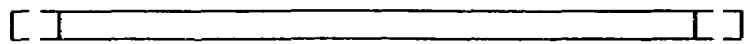
Figure 4:
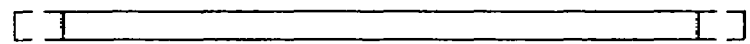
Figure 5:
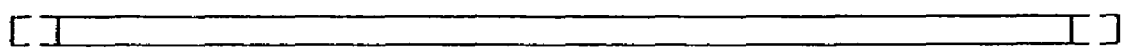
Figure 6:
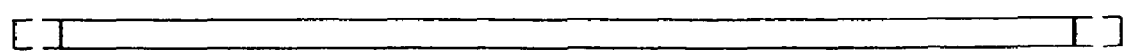

FIG. 1: is a top plan view of a multi-well platform,

FIG. 2: is a bottom plan view thereof,

FIG. 3: is a left elevation view thereof,

FIG. 4: is a right elevation view thereof,

FIG. 5: is a front elevation view thereof,

FIG. 6: is a back elevation view thereof, and

FIG. 7: is a top, front, and right perspective view thereof.

B. Platform for a Multi Well Field

Figure 8:
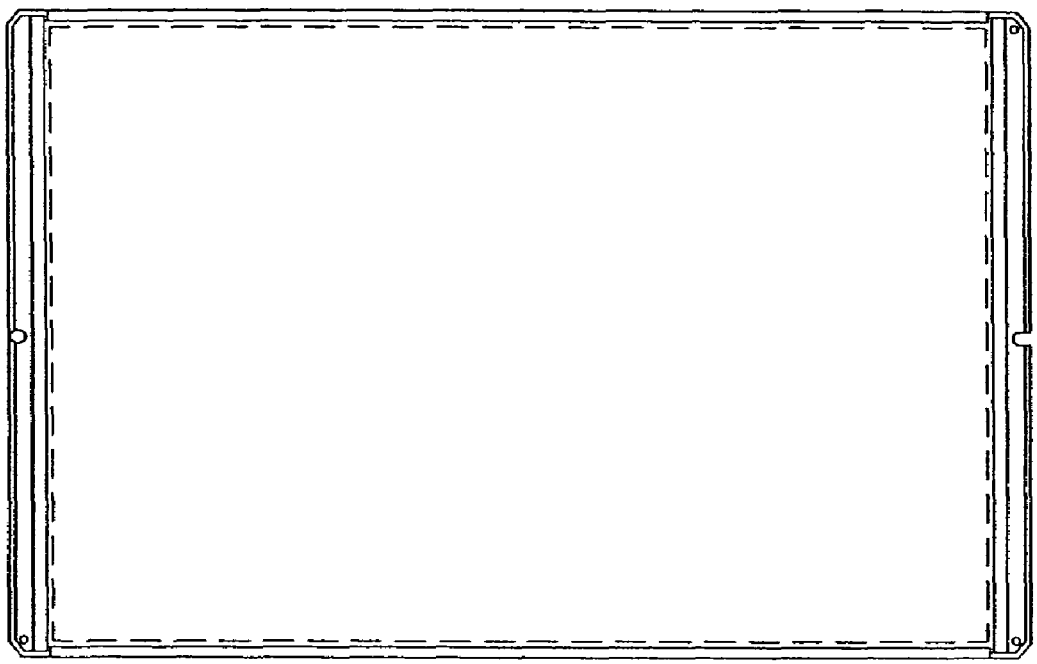
Figure 9:
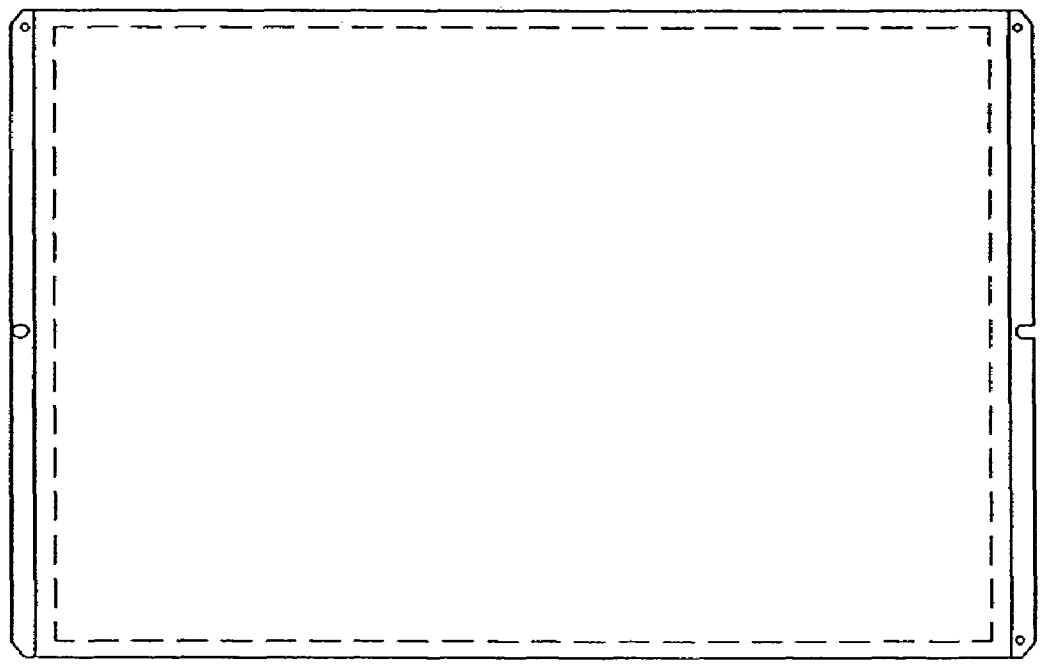
Figure 10:
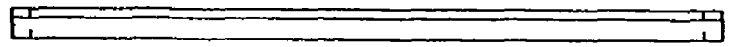
Figure 11:
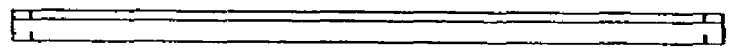
Figure 12:
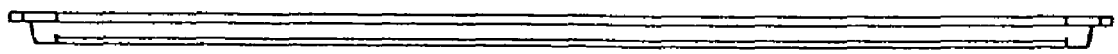
Figure 13:
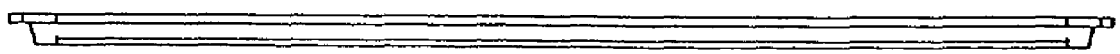

FIG. 8: is a top plan view of a platform for a multi-well field,
FIG. 9: is a bottom plan view thereof,
FIG. 10: is a left elevation view thereof,
FIG. 11: is a right elevation view thereof,
FIG. 12: is a front elevation view thereof,
FIG. 13: is a back elevation view thereof, and
FIG. 14: is a top, front, and right perspective view thereof

C. Platform for a Multi Well Field

Figure 15:
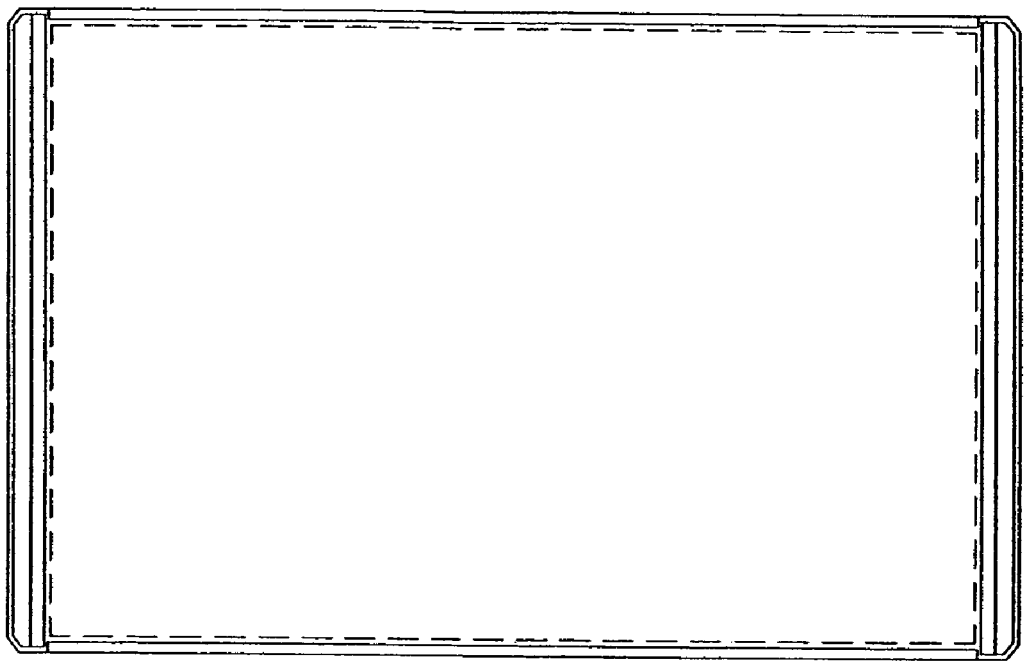
Figure 16:
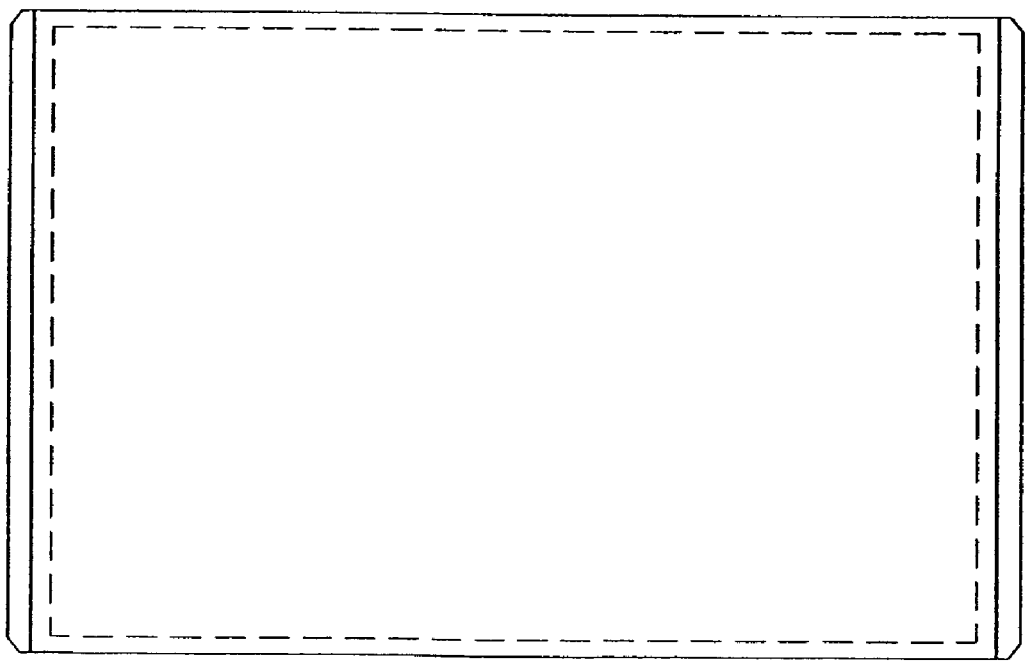
Figure 17:
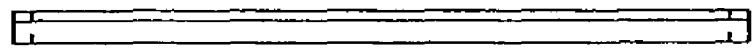
Figure 18:
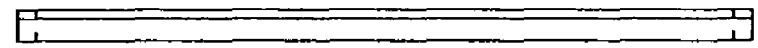
Figure 19:
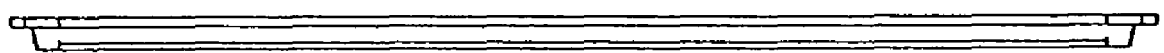
Figure 20:
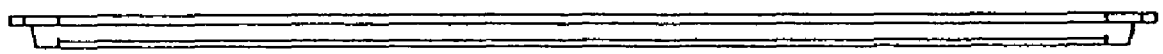

FIG. 15: is a top plan view of a platform for a multi-well field,
FIG. 16: is a bottom plan view thereof,
FIG. 17: is a left elevation view thereof,
FIG. 18: is a right elevation view thereof,
FIG. 19: is a front elevation view thereof,
FIG. 20: is a back elevation view thereof, and
FIG. 21: is a top, front, and right perspective view thereof.

D. Platform for a Multi Well Field

Figure 22:
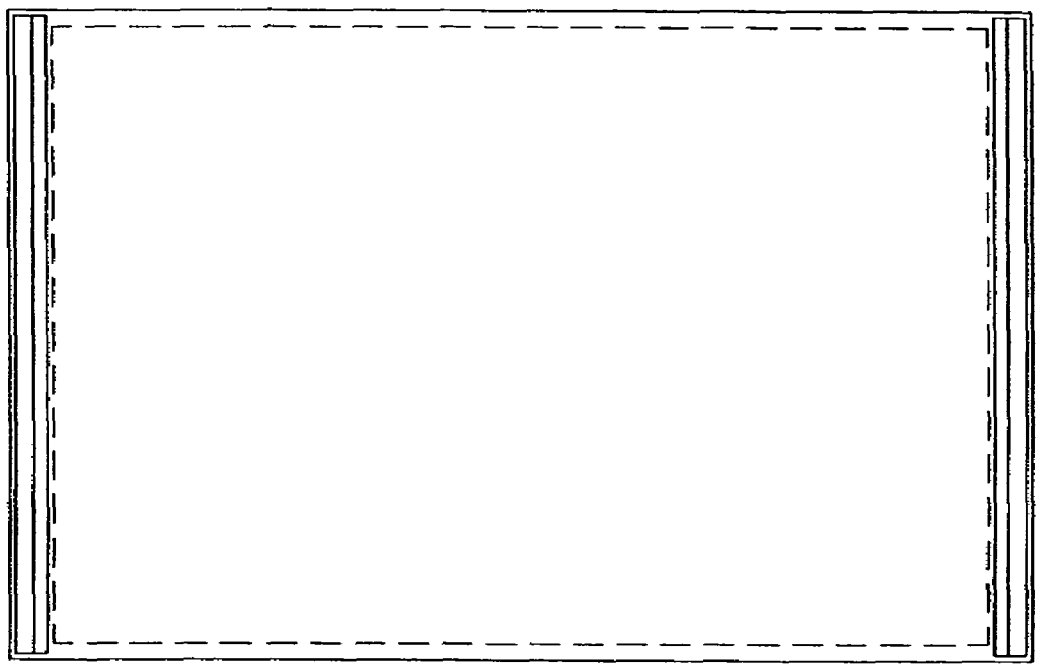
Figure 23:
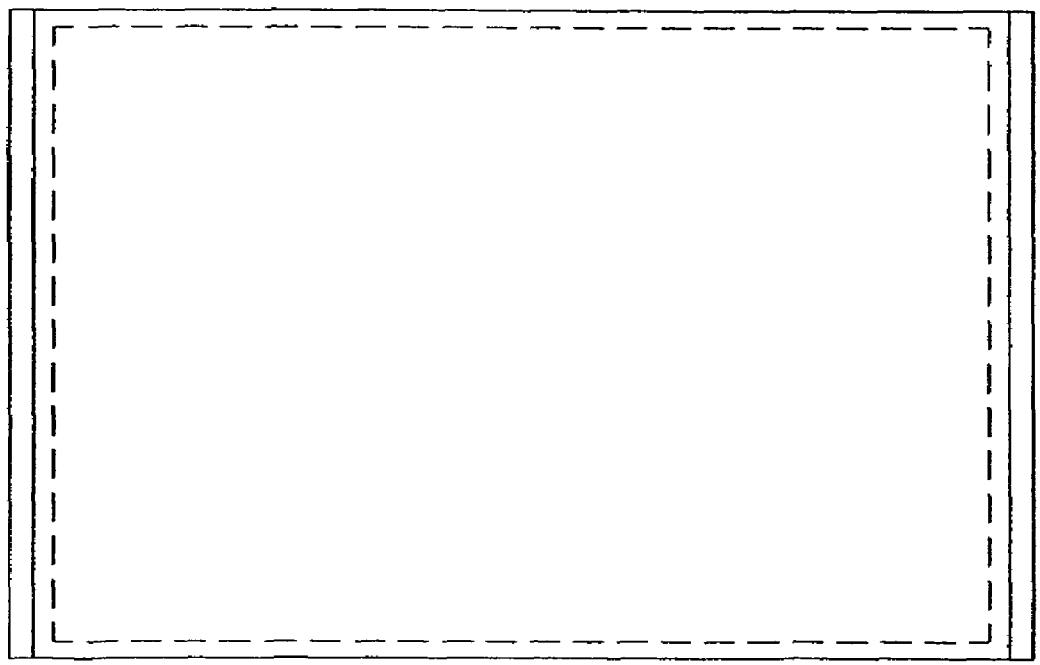
Figure 24:
Figure 25:
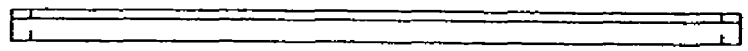
Figure 26:
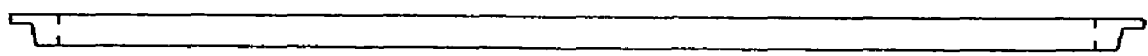
Figure 27:
Figure 28:
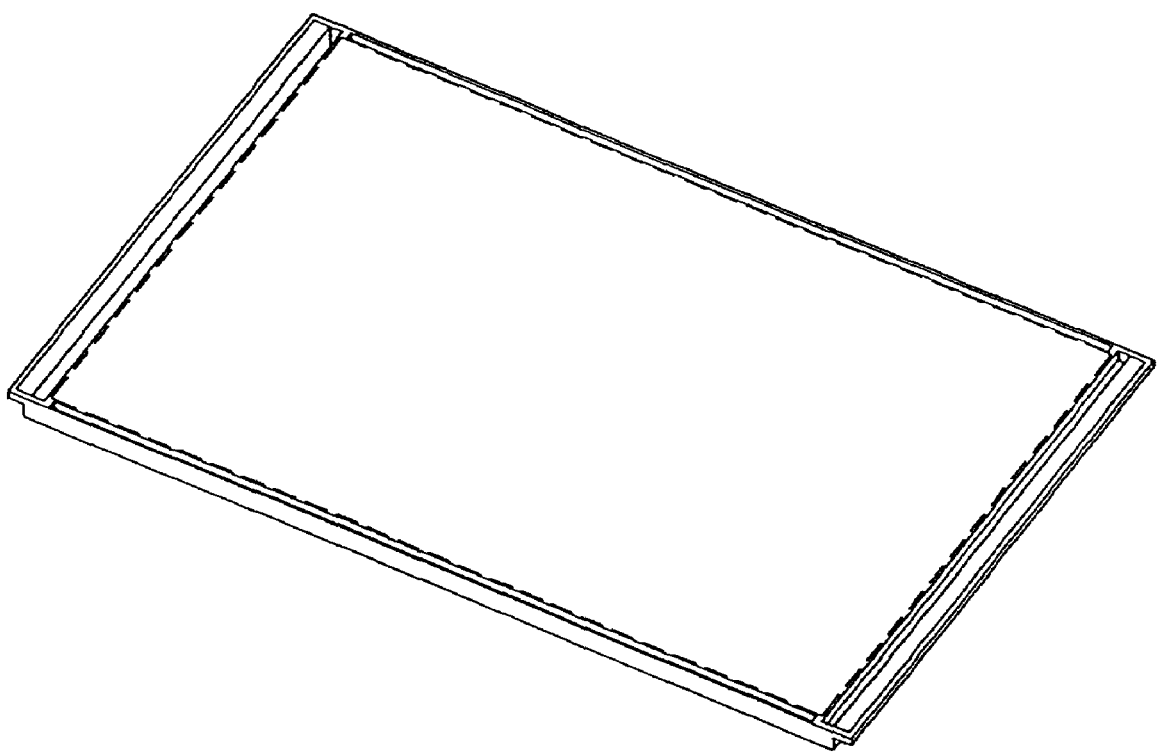

FIG. 22: is a top plan view of a platform for a multi-well field,
FIG. 23: is a bottom plan view thereof,
FIG. 24: is a left elevation view thereof,
FIG. 25: is a right elevation view thereof,
FIG. 26: is a front elevation view thereof,
FIG. 27: is a back elevation view thereof, and
FIG. 28: is a top, front, and right perspective view thereof.

E. Platform for a Multi Well Field

Figure 29:
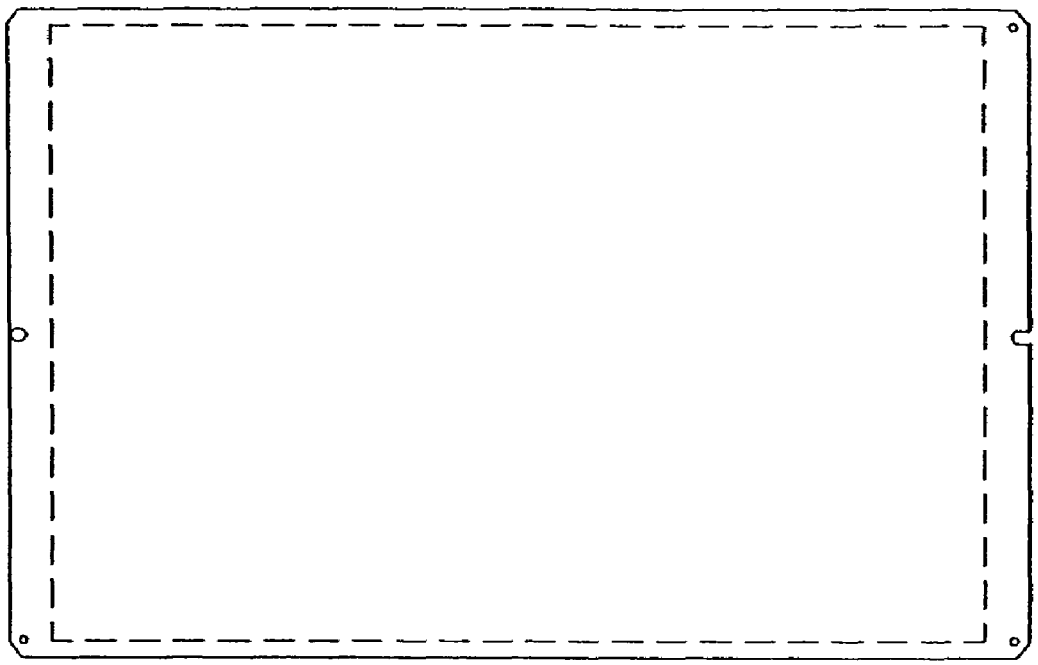
Figure 30:
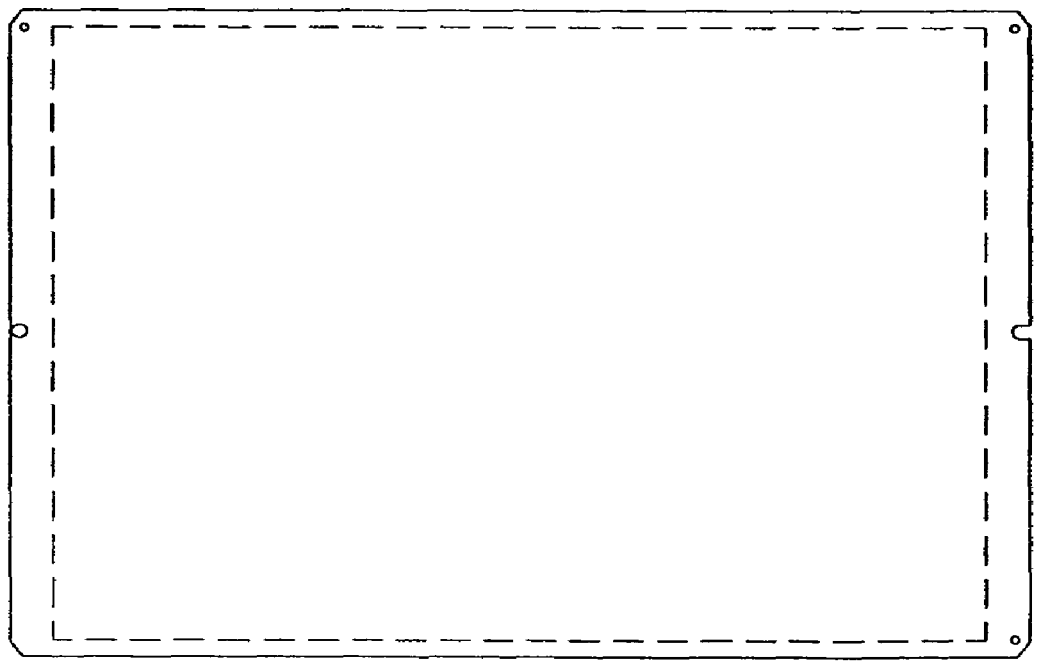
Figure 31:
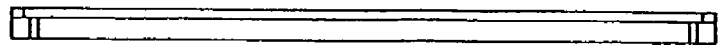
Figure 32:
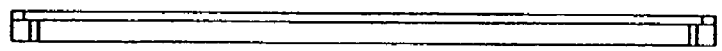
Figure 33:
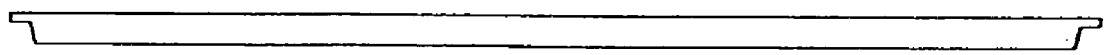
Figure 34:
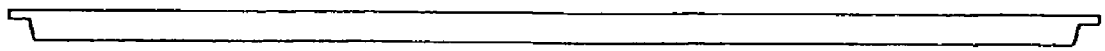
Figure 35:
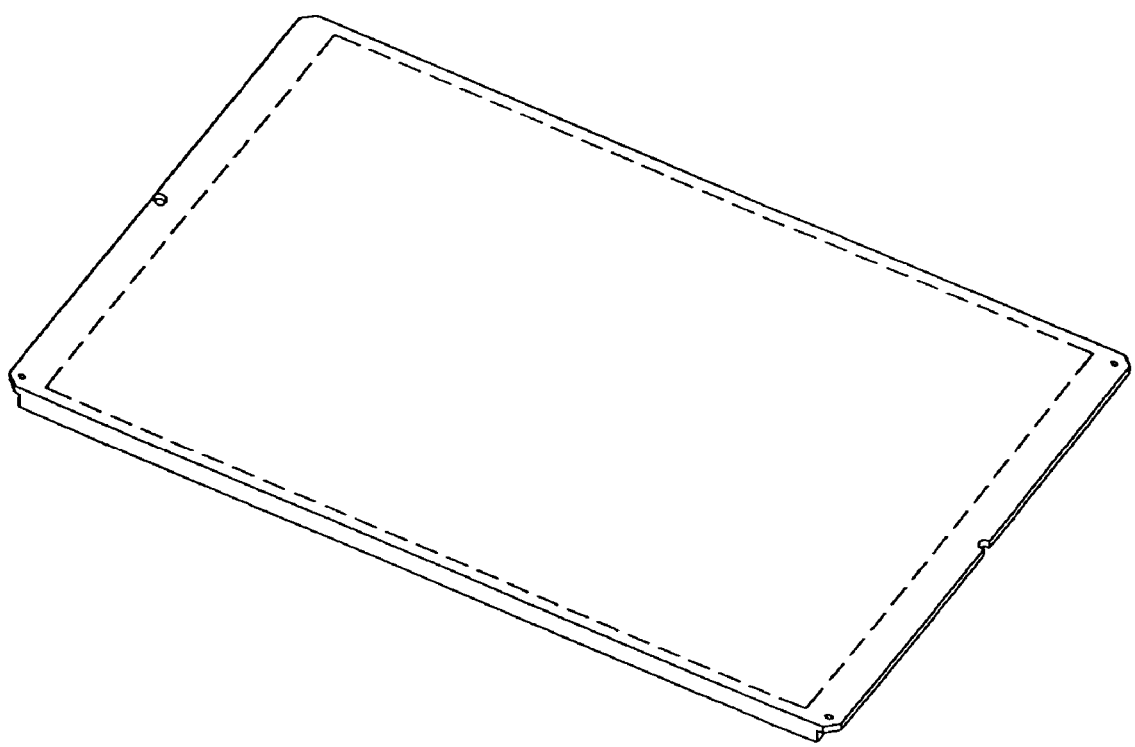

FIG. 29: is a top plan view of a platform for a multi-well field,
FIG. 30: is a bottom plan view thereof,
FIG. 31: is a left elevation view thereof,
FIG. 32: is a right elevation view thereof,
FIG. 33: is a front elevation view thereof,
FIG. 34: is a back elevation view thereof, and
FIG. 35: is a top, front, and right perspective view thereof.

F. Platform for a Multi Well Field

Figure 36:
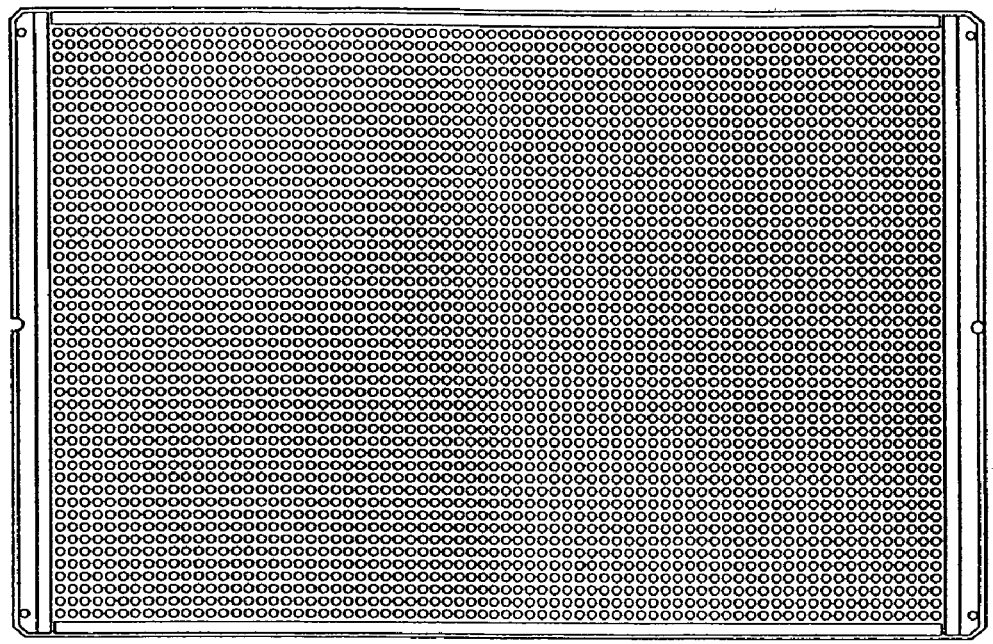
Figure 37:
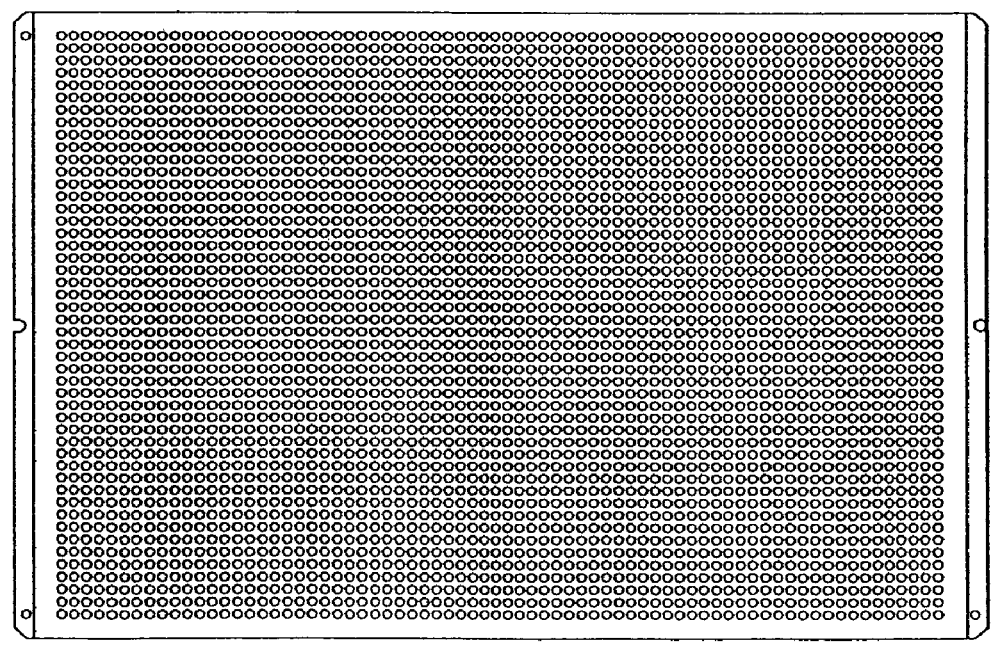
Figure 38:
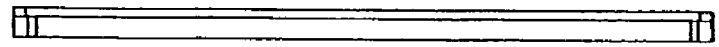
Figure 39:
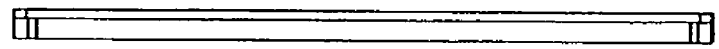
Figure 40:
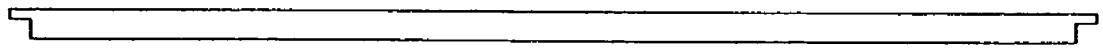
Figure 41:
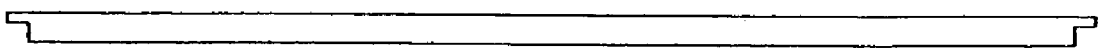
Figure 42:
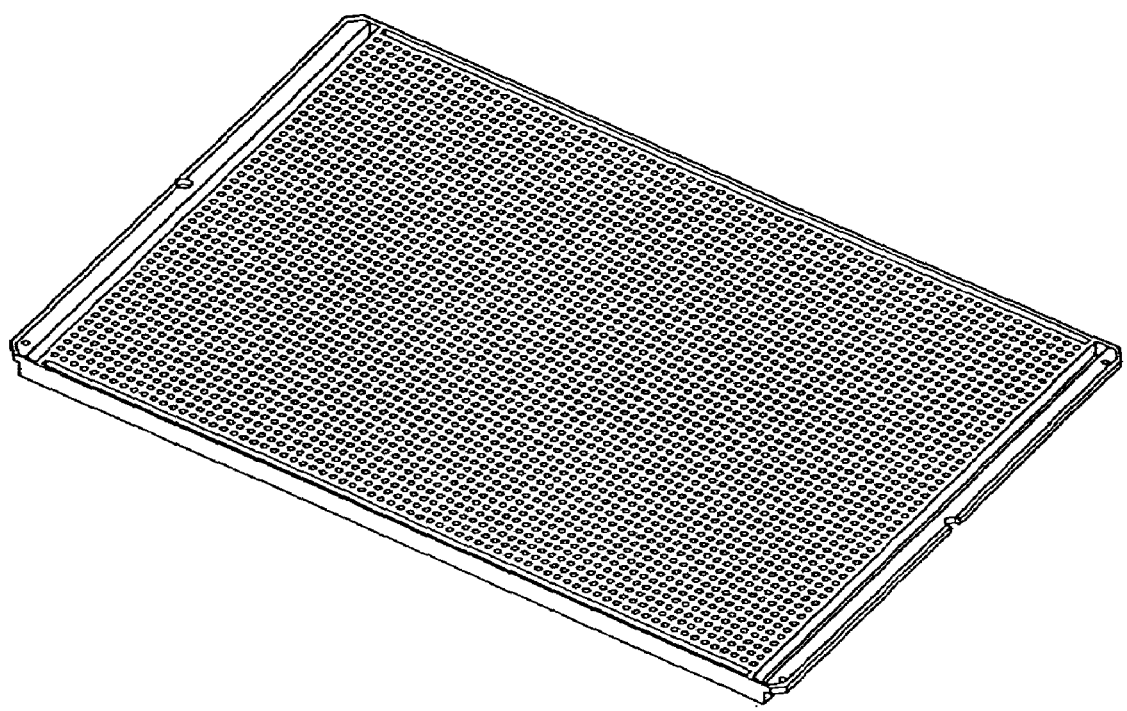

FIG. 36: is a top plan view of a platform for a multi-well field,
FIG. 37: is a bottom plan view thereof,
FIG. 38: is a left elevation view thereof,
FIG. 39: is a right elevation view thereof,
FIG. 40: is a front elevation view thereof,
FIG. 41: is a back elevation view thereof, and
FIG. 42: is a top, front, and right perspective view thereof.

G. Multi Well Platform Having 3,456 Wells

Figure 43:
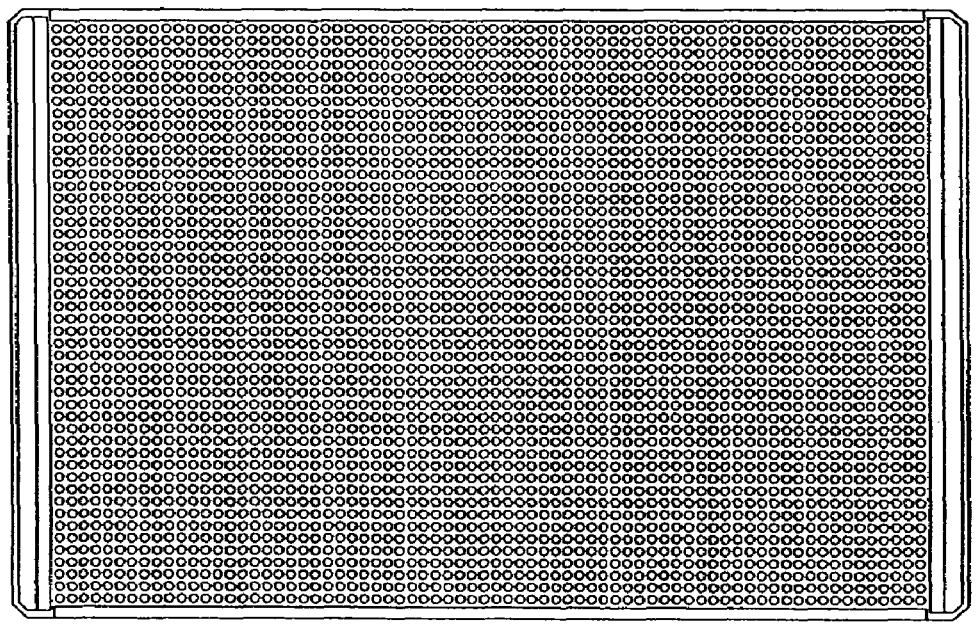
Figure 44:
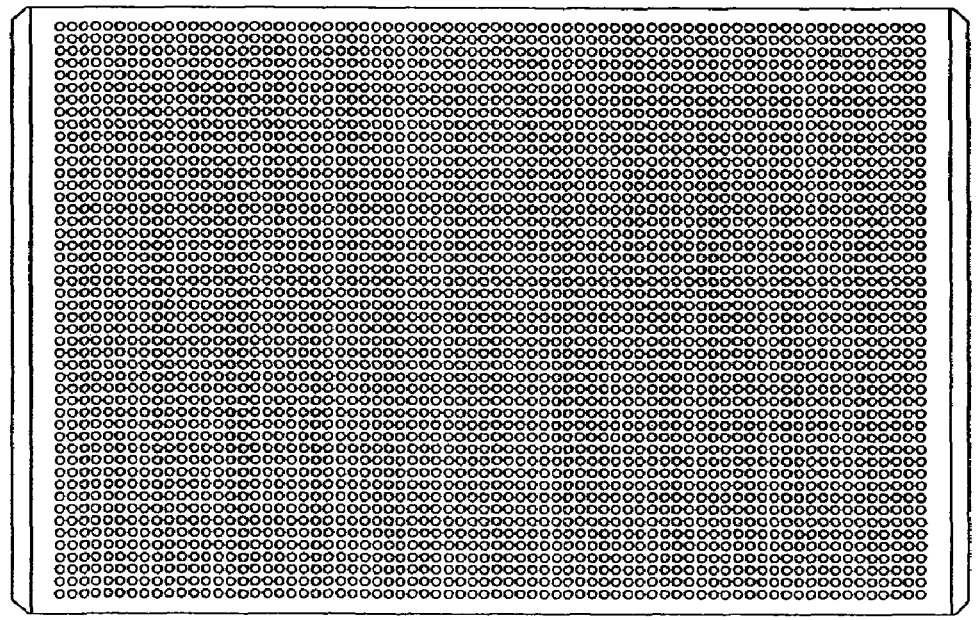
Figure 45:
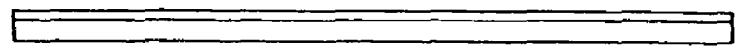
Figure 46:
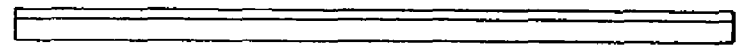
Figure 47:
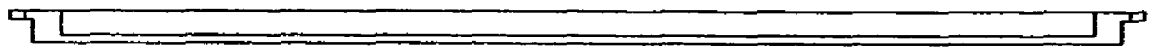
Figure 48:
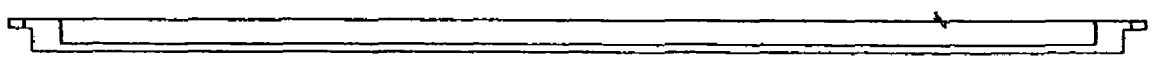

FIG. 43: is a top plan view of a multi-well platform having 3,456 wells,
FIG. 44: is a bottom plan view thereof,
FIG. 45: is a left elevation view thereof,
FIG. 46: is a right elevation view thereof,
FIG. 47: is a front elevation view thereof,
FIG. 48: is a back elevation view thereof, and
FIG. 49: is a top, front, and right perspective view thereof.

H. Multi Well Platform Having 3,456 Wells

Figure 50:
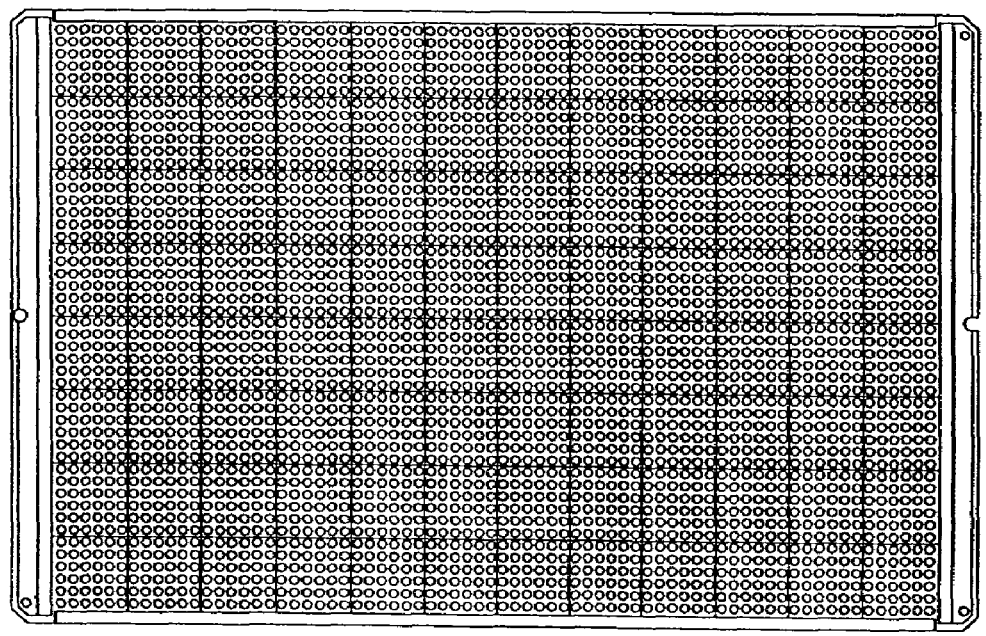
Figure 51:
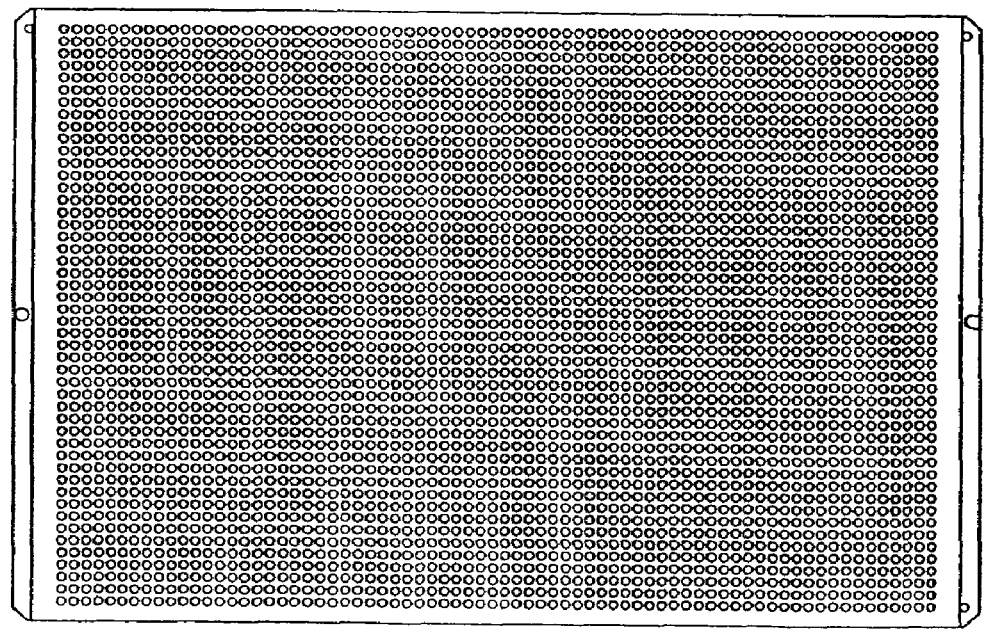
Figure 52:
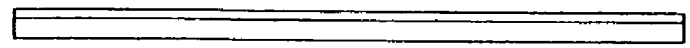
Figure 53:
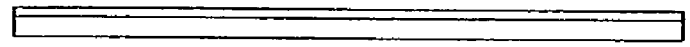
Figure 54:
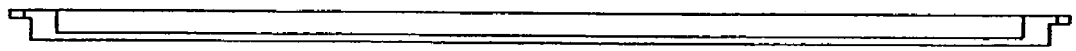
Figure 55:
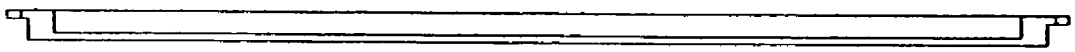

FIG. 50: is a top plan view of a multi-well platform having 3,456 wells,
FIG. 51: is a bottom plan view thereof,
FIG. 52: is a left elevation view thereof,
FIG. 53: is a right elevation view thereof,
FIG. 54: is a front elevation view thereof,
FIG. 55: is a back elevation view thereof, and
FIG. 56: is a top, front, and right perspective view thereof.

I. Lid for a Multi Well Platform

Figure 57:
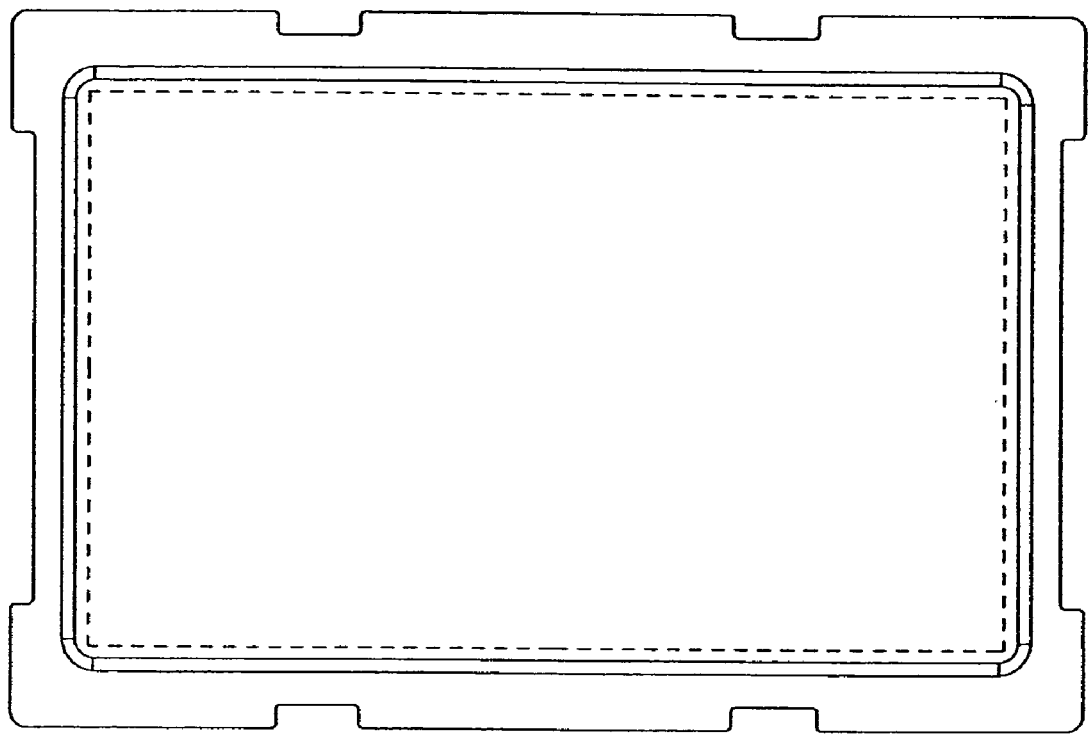
Figure 58:
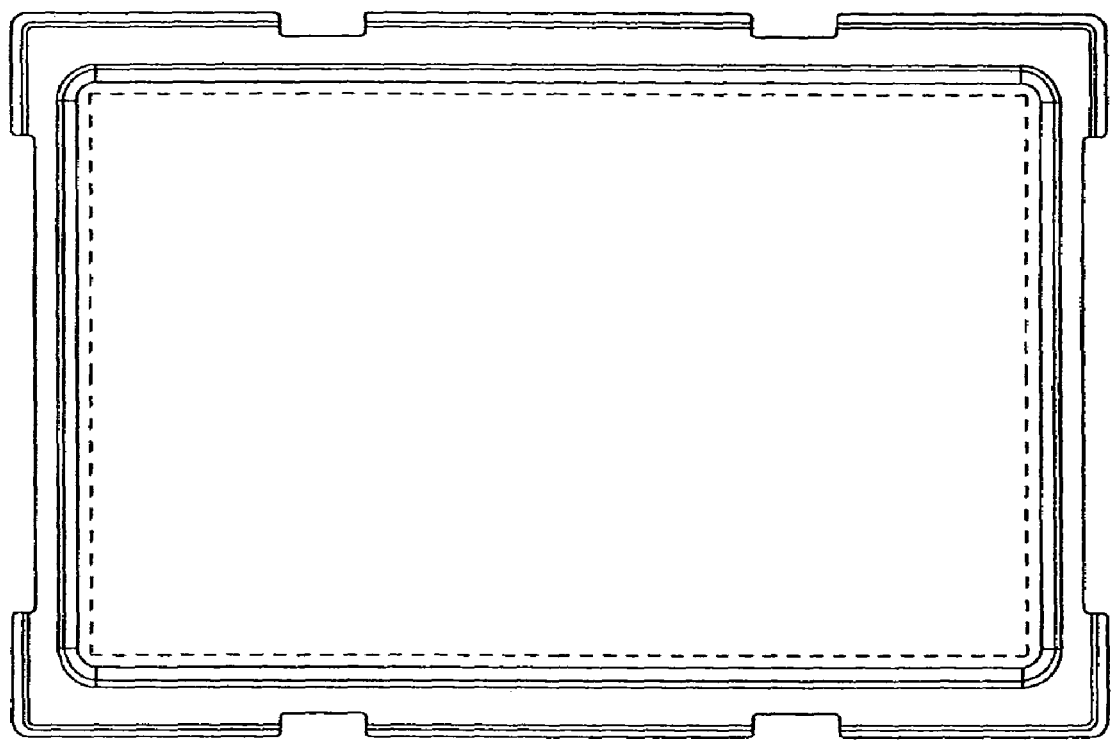
Figure 59:
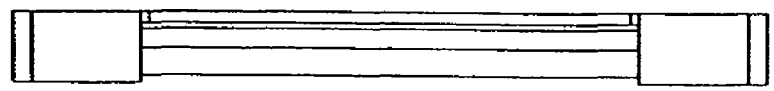
Figure 60:
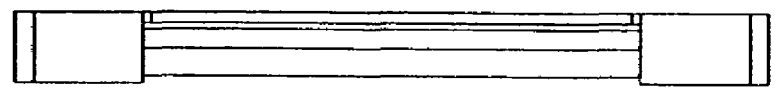
Figure 61:
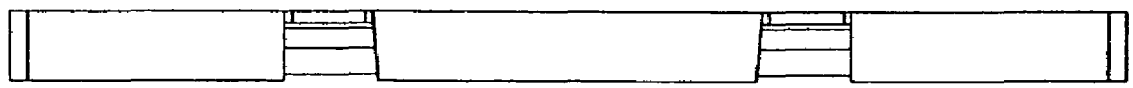
Figure 62:
Figure 63:
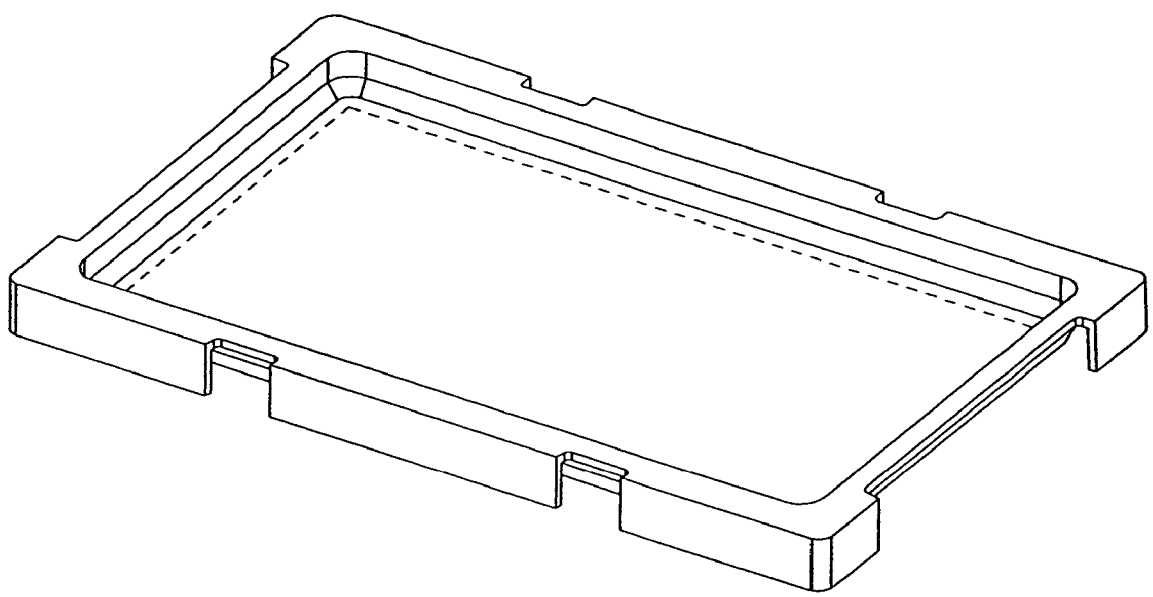

FIG. 57: is a top plan view of a lid for a multi-well platform,
FIG. 58: is a bottom plan view thereof,
FIG. 59: is a left elevation view thereof,
FIG. 60: is a right elevation view thereof,
FIG. 61: is a front elevation view thereof,
FIG. 62: is a back elevation view thereof, and
FIG. 63: is a top, front, and right perspective view thereof.

J. Lid for a Multi Well Platform

Figure 64:
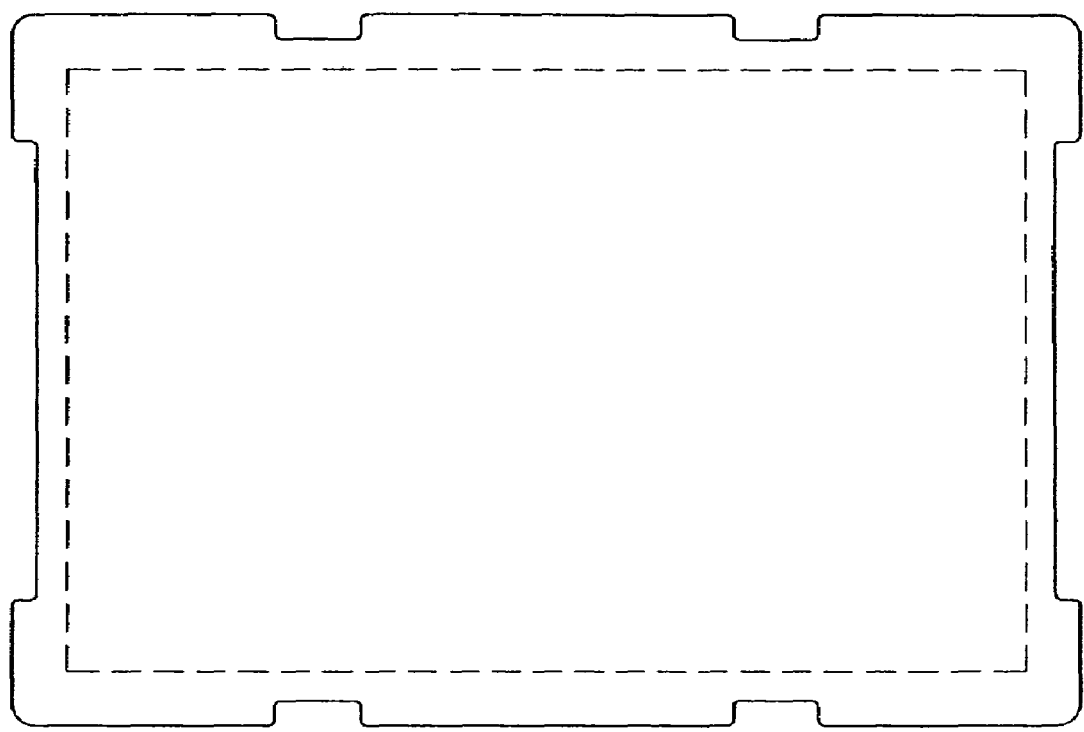
Figure 65:
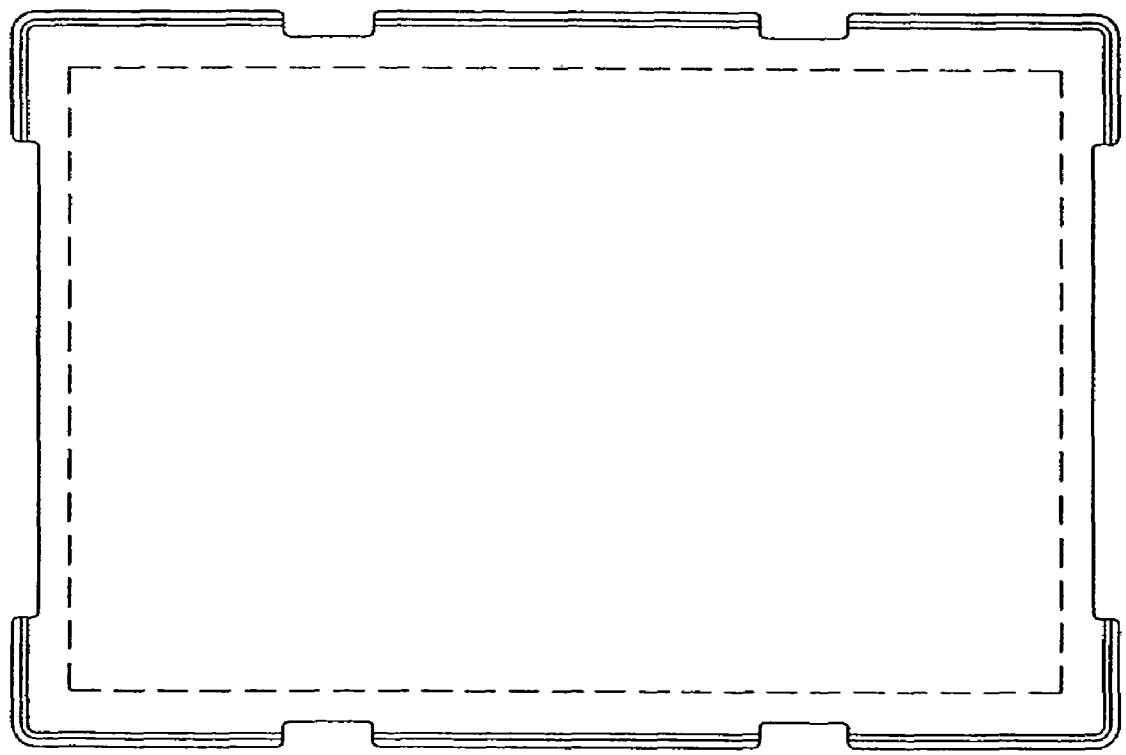
Figure 66:
Figure 67:
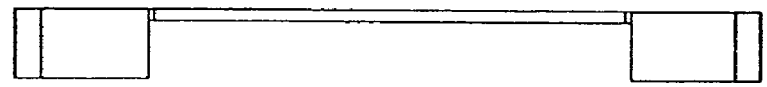
Figure 68:
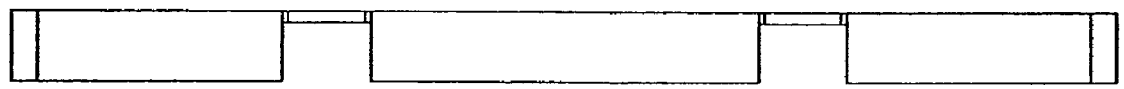
Figure 69:
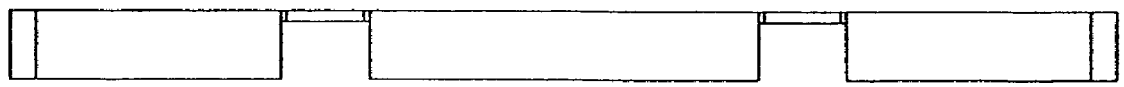
Figure 70:
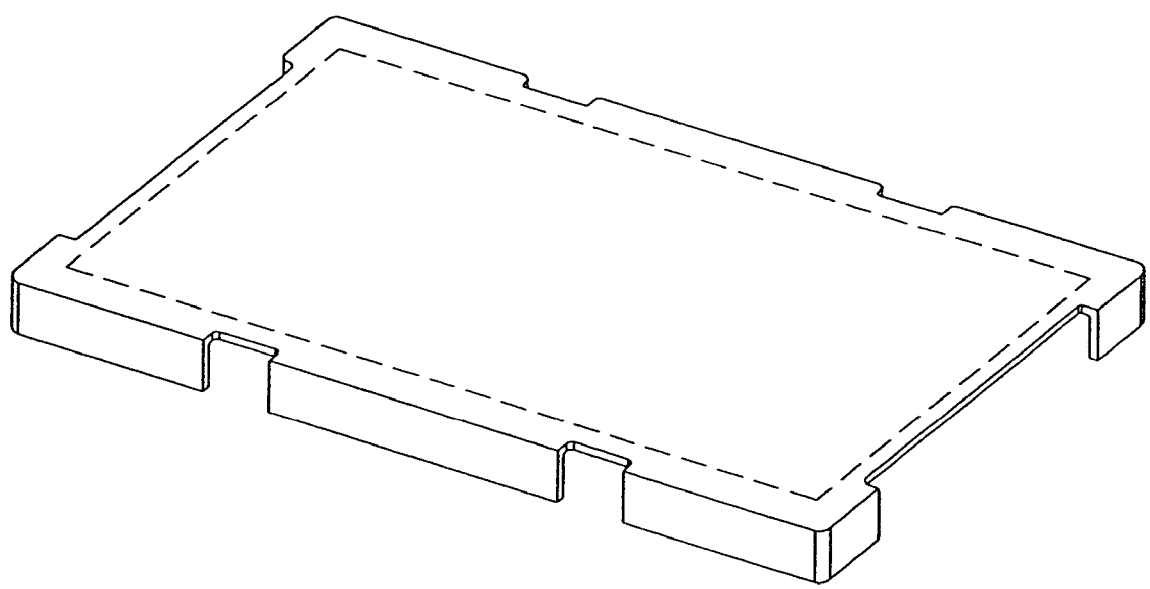

FIG. 64: is a top plan view of a lid for a multi-well platform,
FIG. 65: is a bottom plan view thereof,
FIG. 66: is a left elevation view thereof,
FIG. 67: is a right elevation view thereof,
FIG. 68: is a front elevation view thereof,
FIG. 69: is a back elevation view thereof, and
FIG. 70: is a top, front, and right perspective view thereof.

K. Lid for a Multi Well Platform

Figure 71:
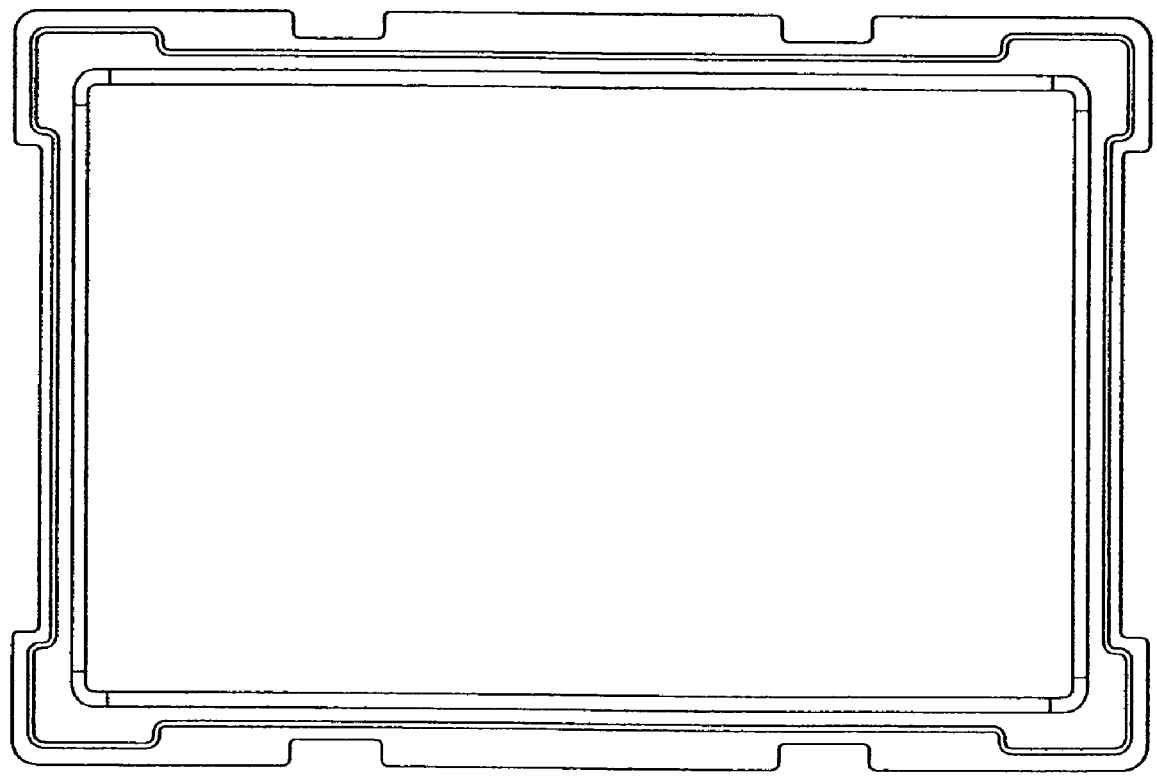
Figure 72:
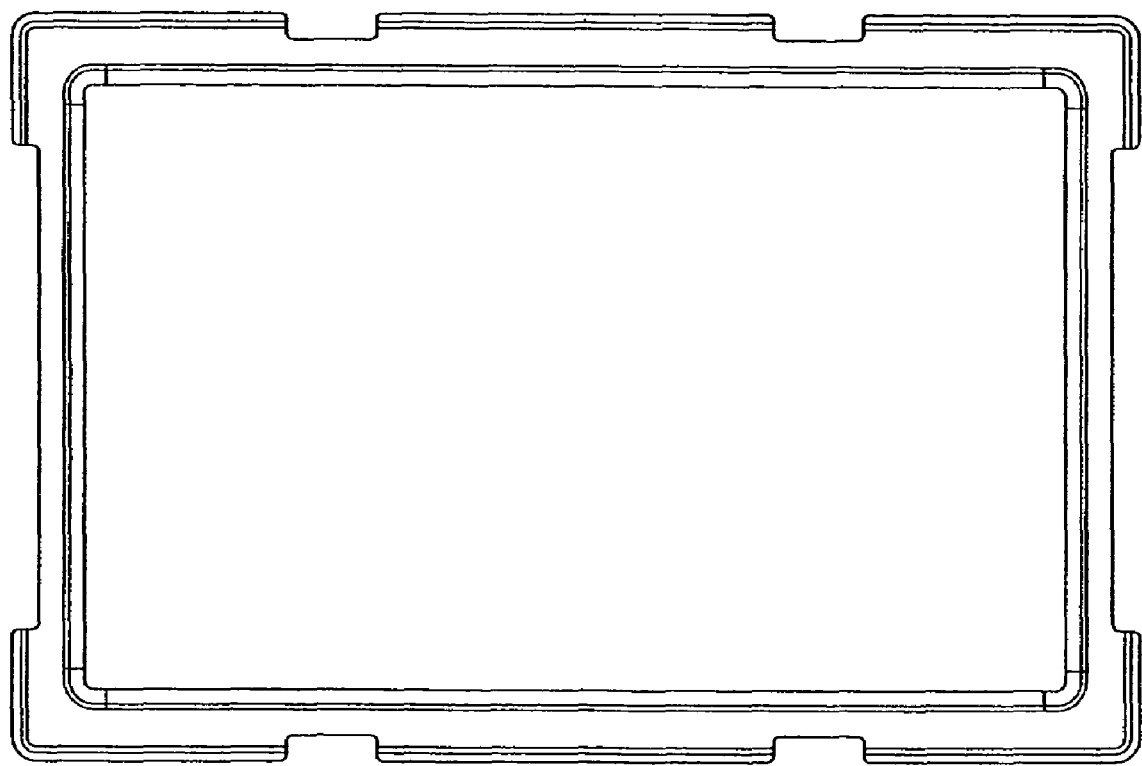
Figure 73:
Figure 74:
Figure 75:
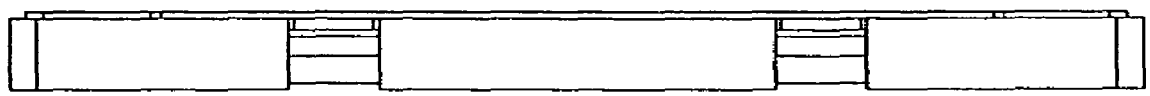
Figure 76:
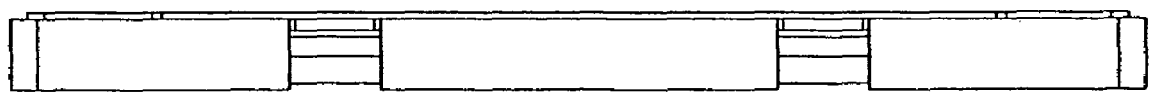
Figure 77:
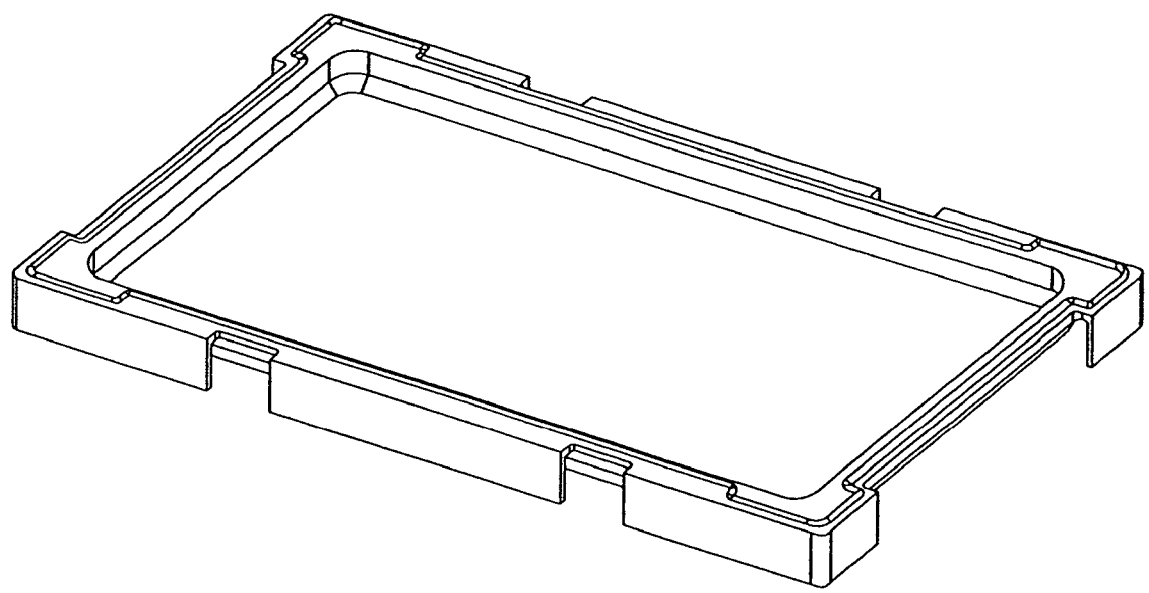

FIG. 71: is a top plan view of a lid for a multi-well platform,
FIG. 72: is a bottom plan view thereof,
FIG. 73: is a left elevation view thereof,
FIG. 74: is a right elevation view thereof,
FIG. 75: is a front elevation view thereof,
FIG. 76: is a back elevation view thereof, and
FIG. 77: is a top, front, and right perspective view thereof.

L. Lid for a Multi Well Platform

Figure 78:
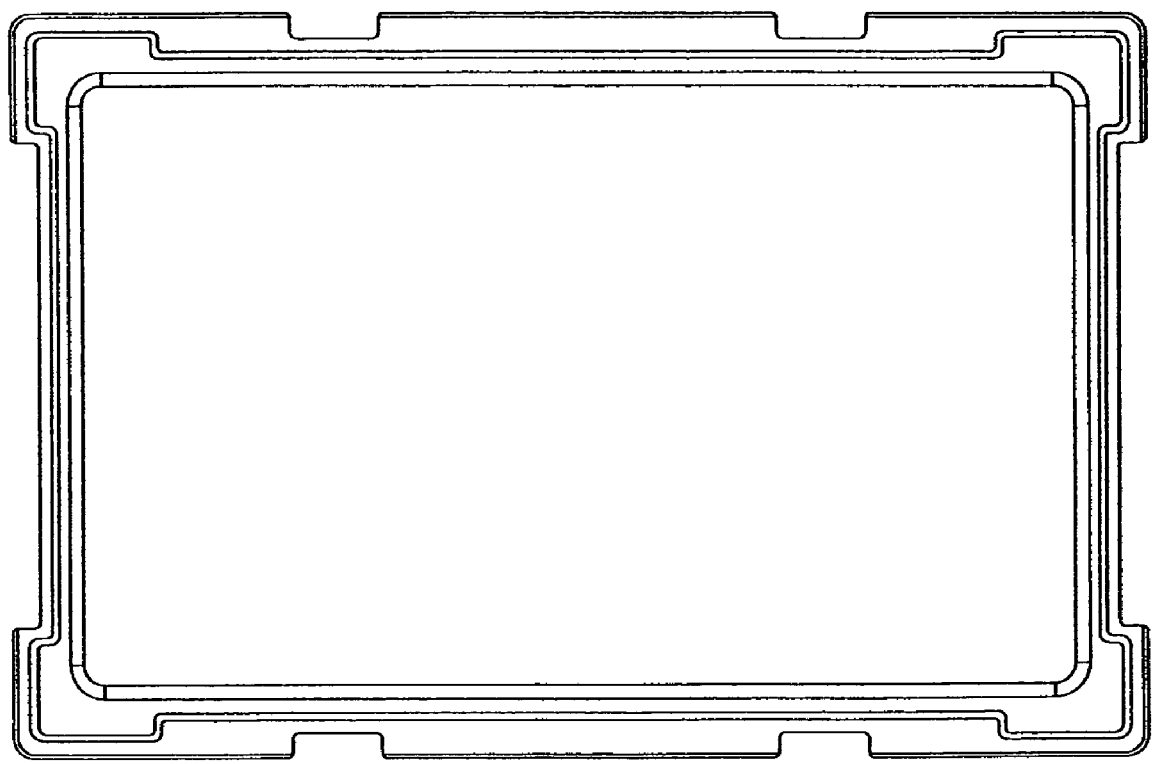
Figure 79:
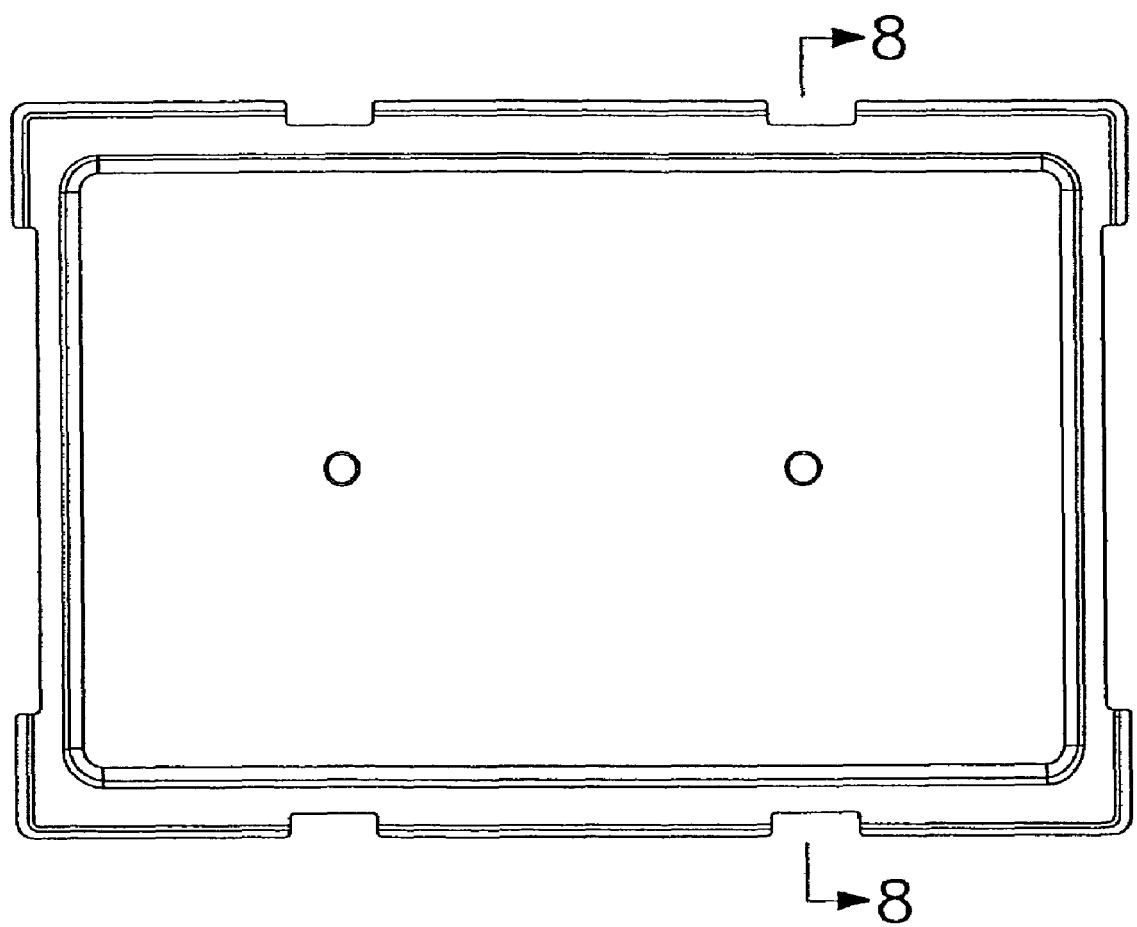
Figure 80:
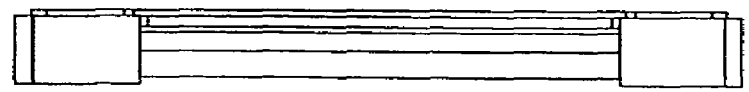
Figure 81:
Figure 82:
Figure 83:
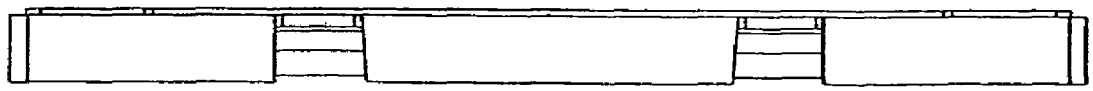
Figure 84:
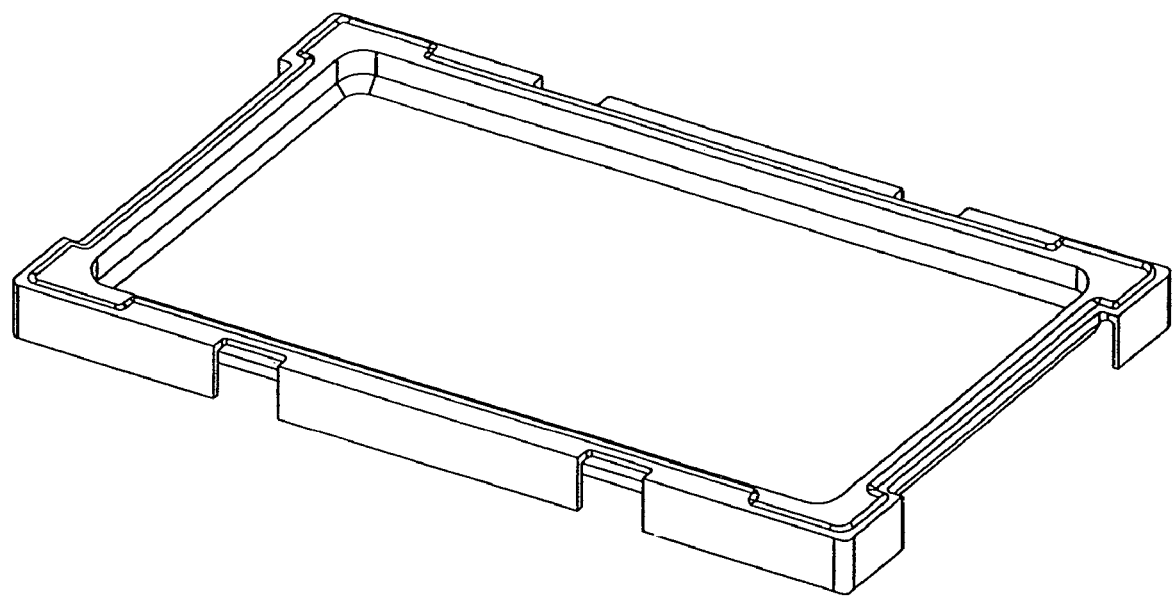
Figure 85:
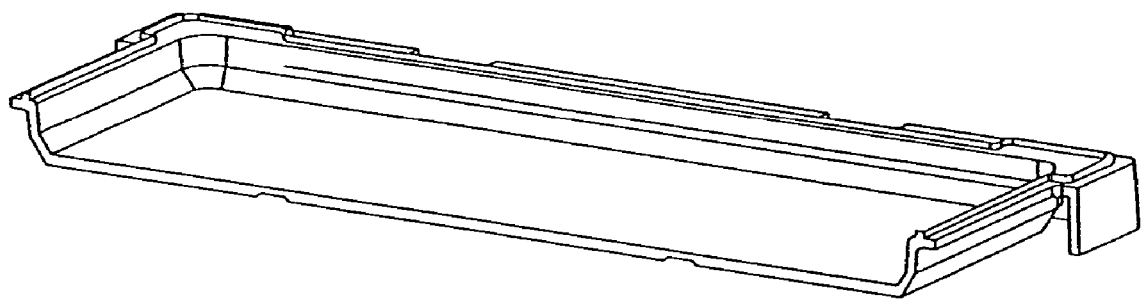

FIG. 78: is a top plan view of a lid for a multi-well platform,
FIG. 79: is a bottom plan view thereof,
FIG. 80: is a left elevation view thereof,
FIG. 81: is a right elevation view thereof,
FIG. 82: is a front elevation view thereof,
FIG. 83: is a back elevation view thereof,
FIG. 84: is a top, front, and right perspective view thereof, and
FIG. 85: is a cross-sectional view along lines 8-8 of FIG. 79.

M. Lid for a Multi Well Platform

Figure 86:
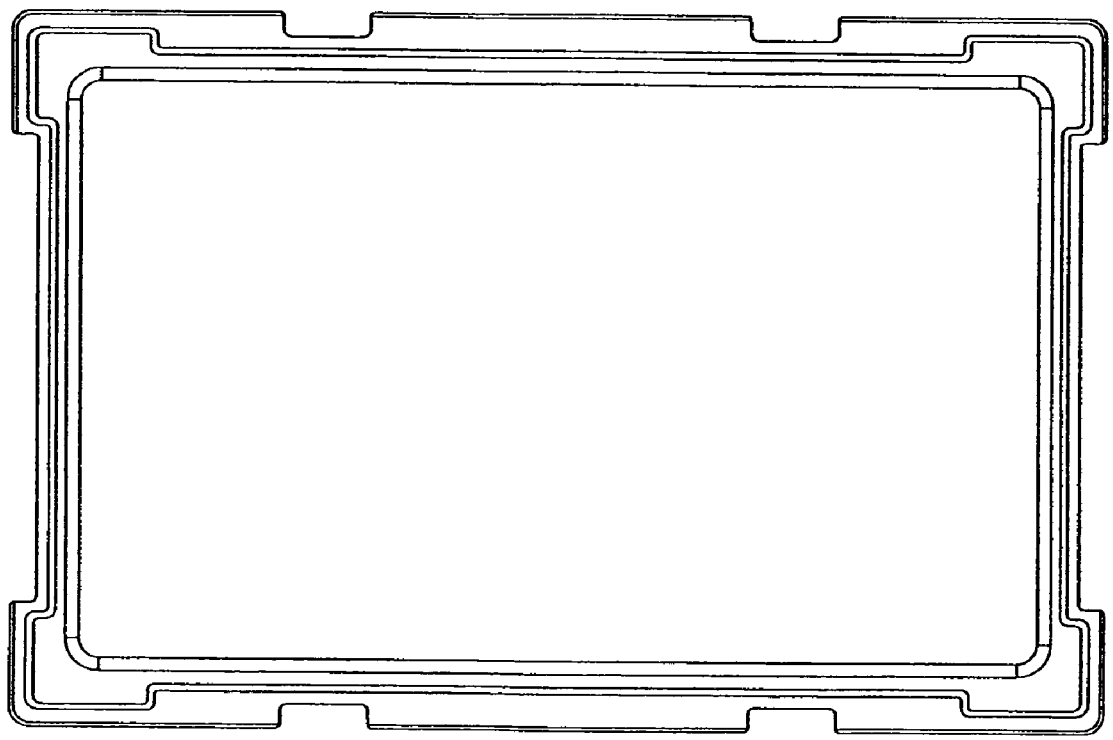
Figure 87:
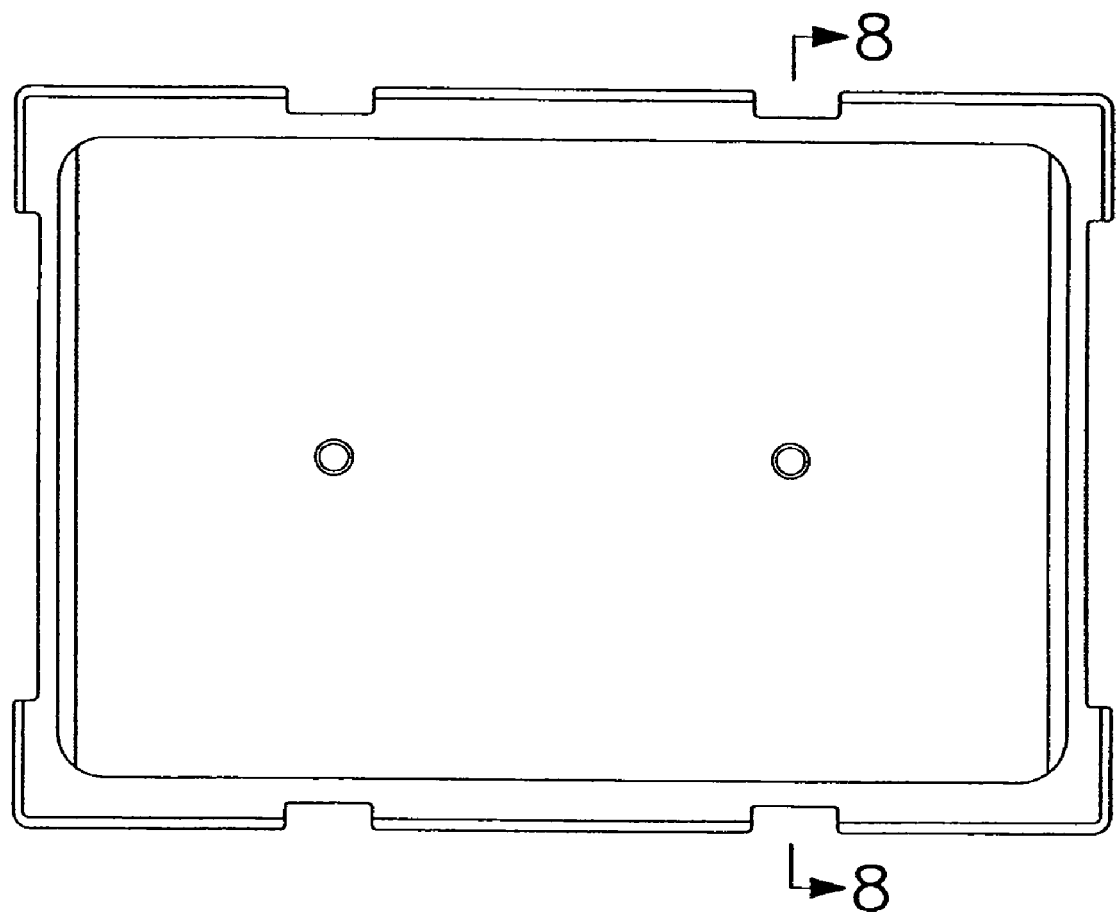
Figure 88:
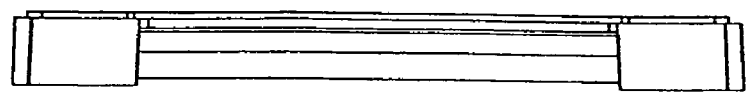
Figure 89:
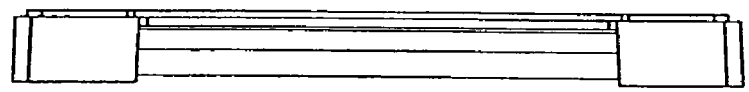
Figure 90:
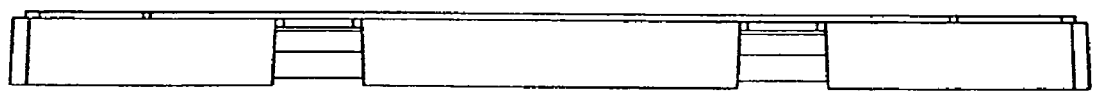
Figure 91:
Figure 92:
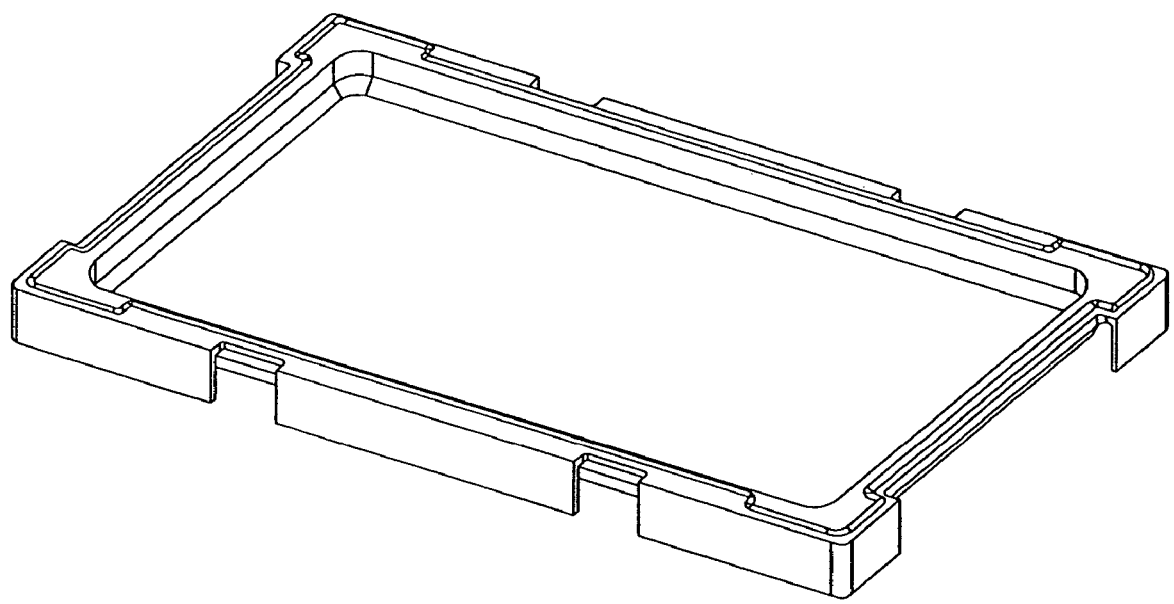
Figure 93:
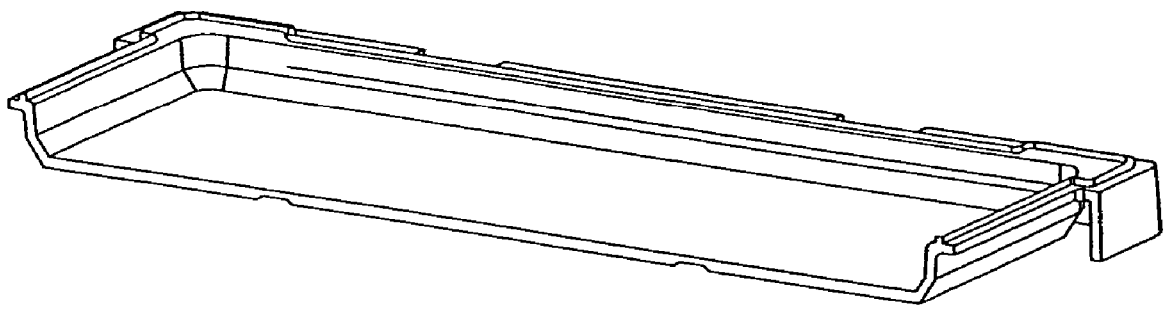

FIG. 86: is a top plan view of a lid for a multi-well platform,
FIG. 87: is a bottom plan view thereof,
FIG. 88: is a left elevation view thereof,
FIG. 89: is a right elevation view thereof,
FIG. 90: is a front elevation view thereof,
FIG. 91: is a back elevation view thereof,
FIG. 92: is a top, front, and right perspective view thereof, and
FIG. 93: is a cross-sectional view along lines 8-8 of FIG. 87.

N. Lid for a Multi Well Platform

Figure 94:
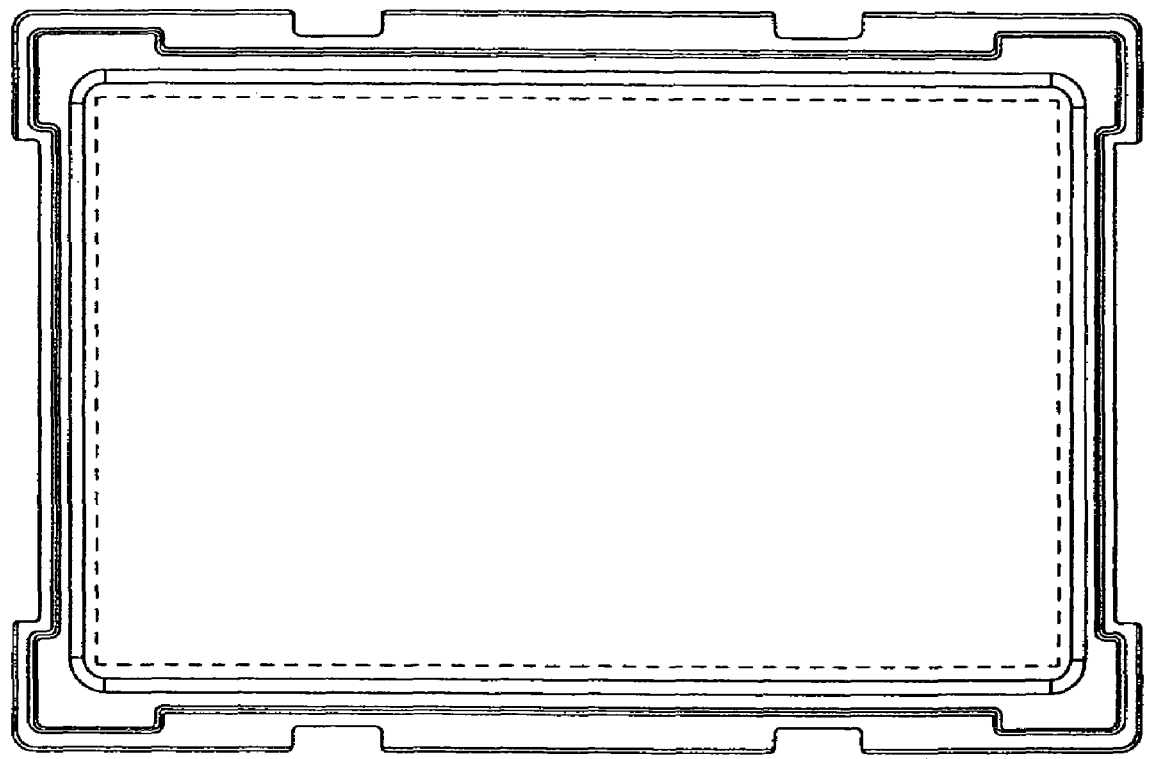
Figure 95:
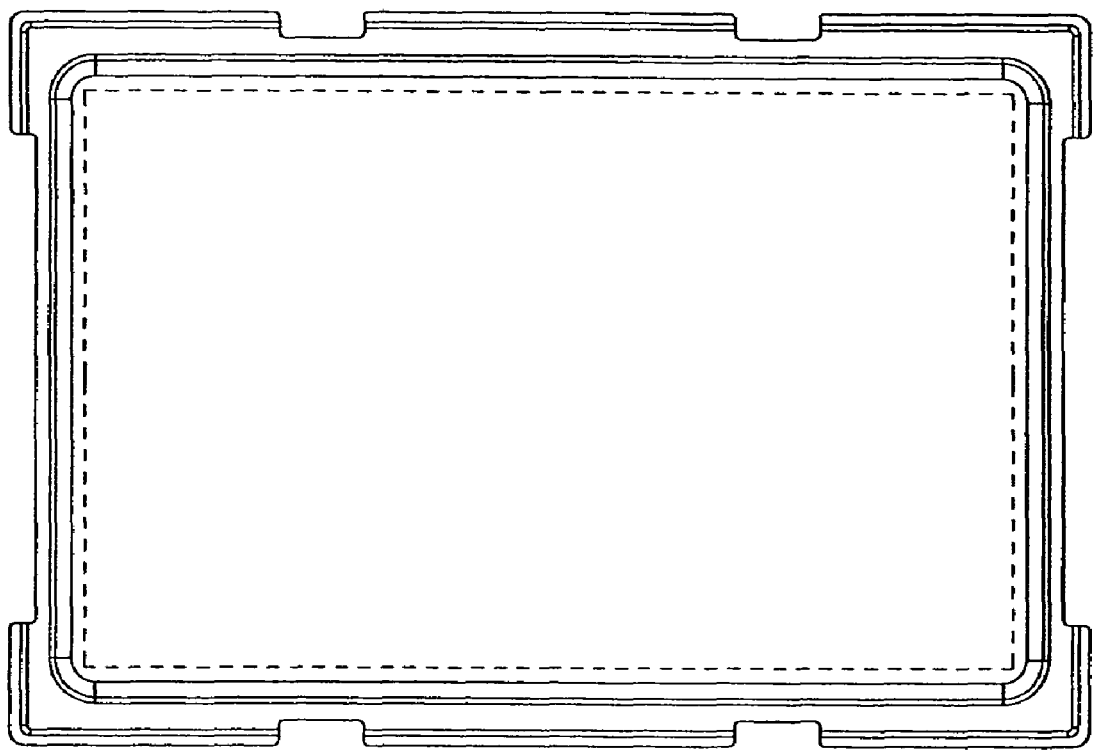
Figure 96:
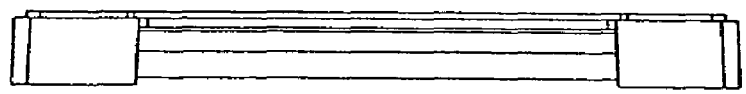
Figure 97:
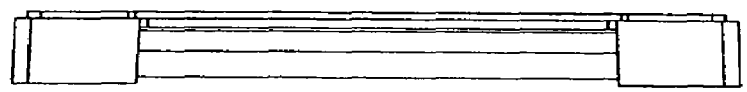
Figure 98:
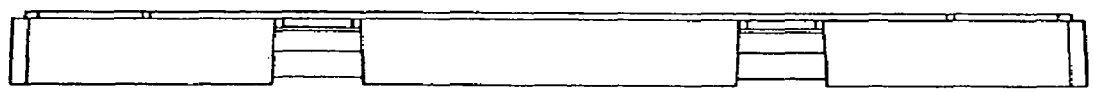
Figure 99:
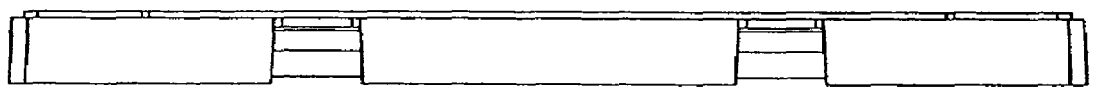
Figure 100:
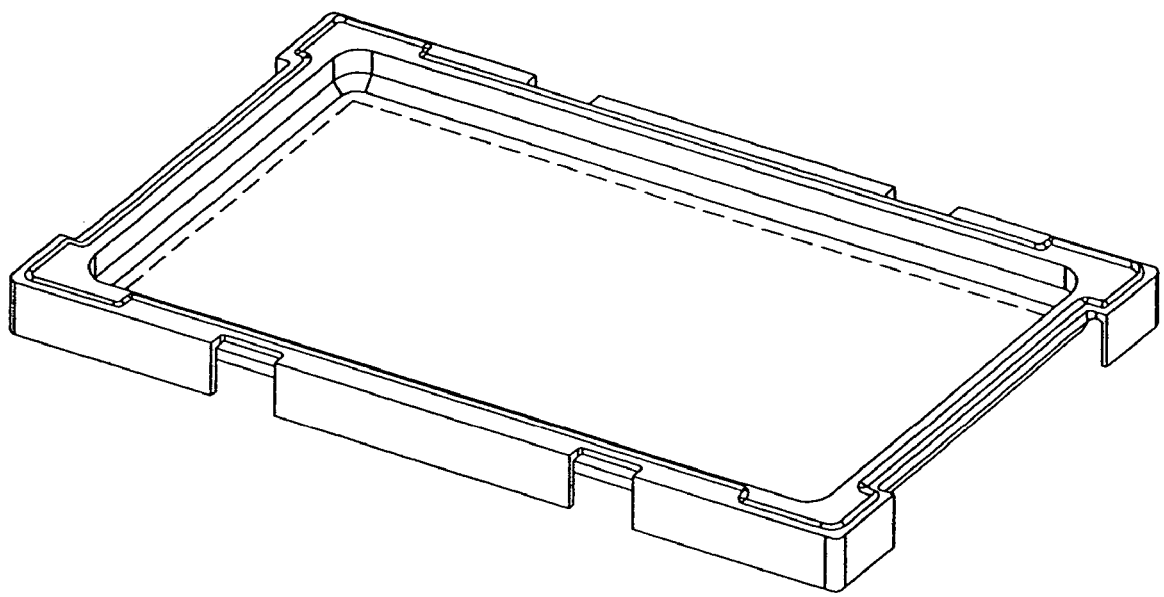

FIG. 94: is a top plan view of a lid for a multi-well platform,
FIG. 95: is a bottom plan view thereof,
FIG. 96: is a left elevation view thereof,
FIG. 97: is a right elevation view thereof,
FIG. 98: is a front elevation view thereof,
FIG. 99: is a back elevation view thereof, and
FIG. 100: is a top, front, and right perspective view thereof.

O. Caddy for a Multi Well Platform

Figure 101:
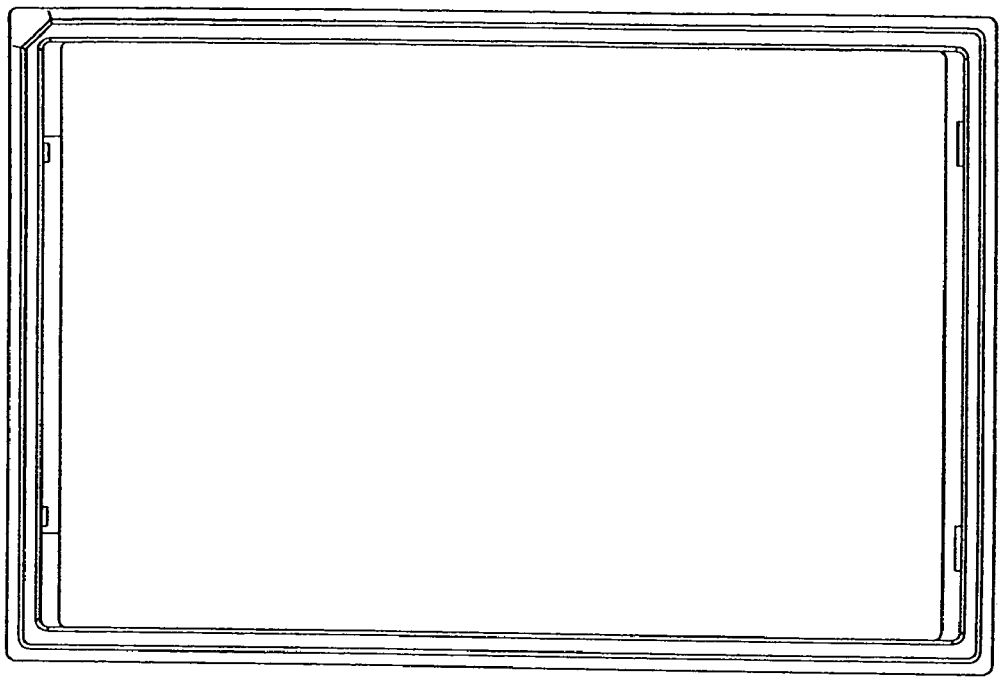
Figure 102:
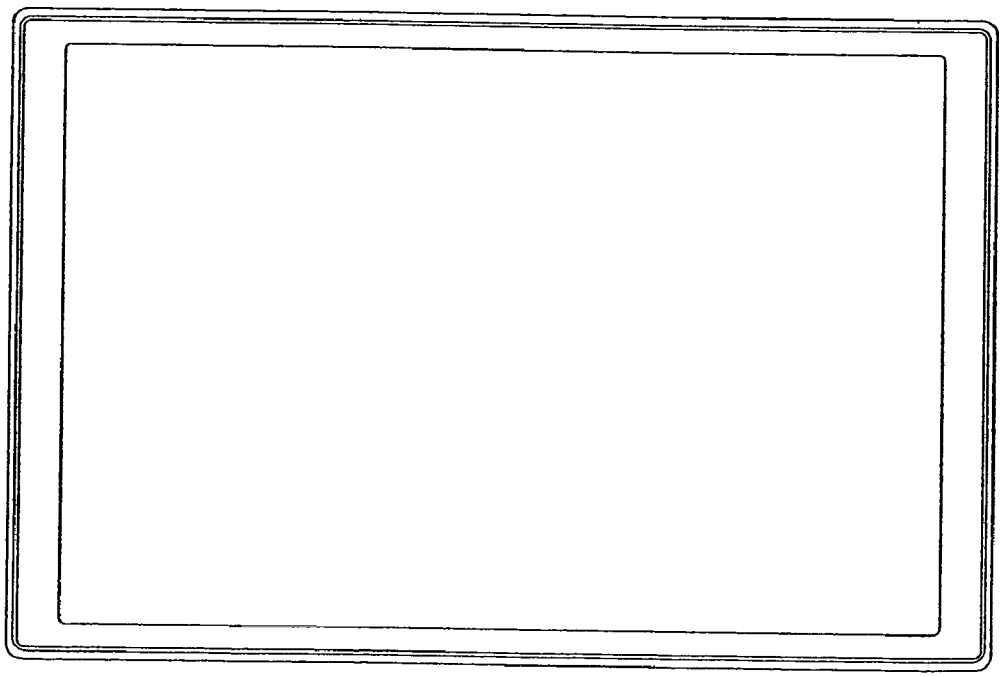
Figure 103:
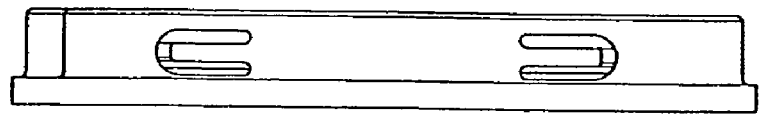
Figure 104:
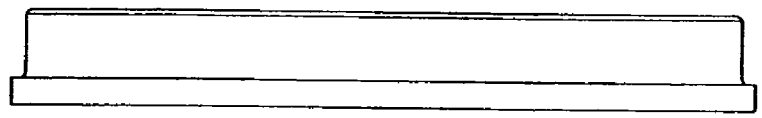
Figure 105:
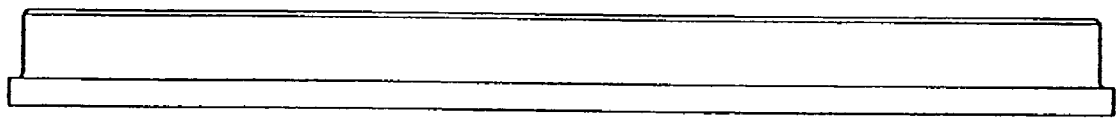
Figure 106:
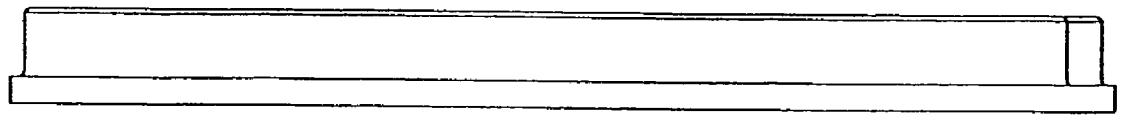
Figure 108:
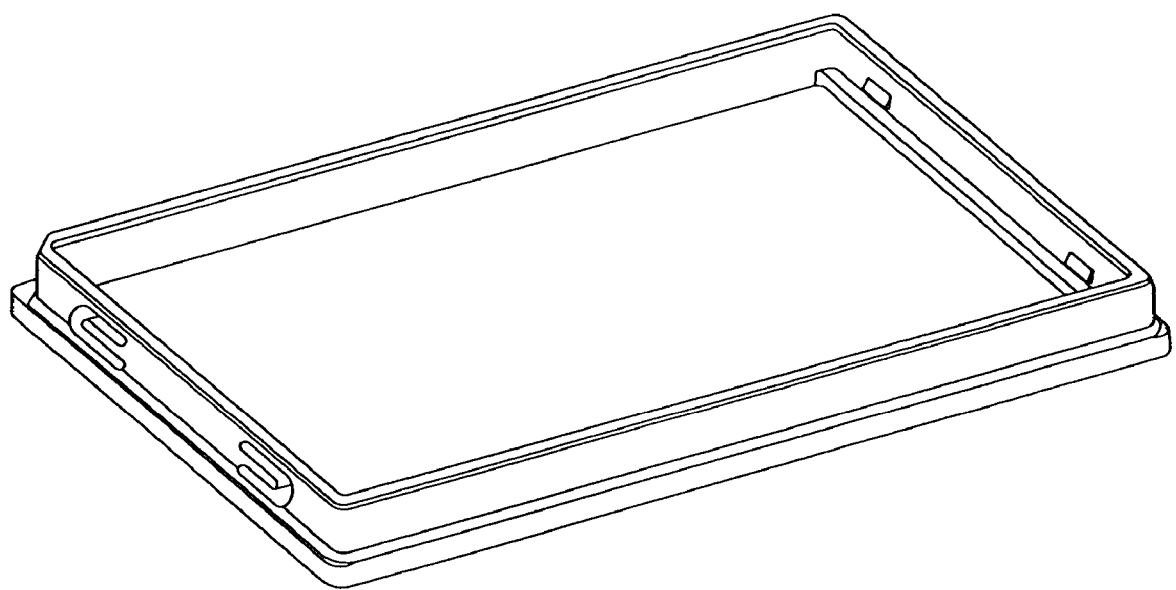

FIG. 101: is a top plan view of a caddy for a multi-well platform,
FIG. 102: is a bottom plan view thereof,
FIG. 103: is a left elevation view thereof,
FIG. 104: is a right elevation view thereof,
FIG. 105: is a front elevation view thereof,
FIG. 106: is a back elevation view thereof,
FIG. 107: is a top, front, and right perspective view thereof, and
FIG. 108: is a top, front, and left perspective view thereof.

P. Caddy for a Multi Well Platform

Figure 109:
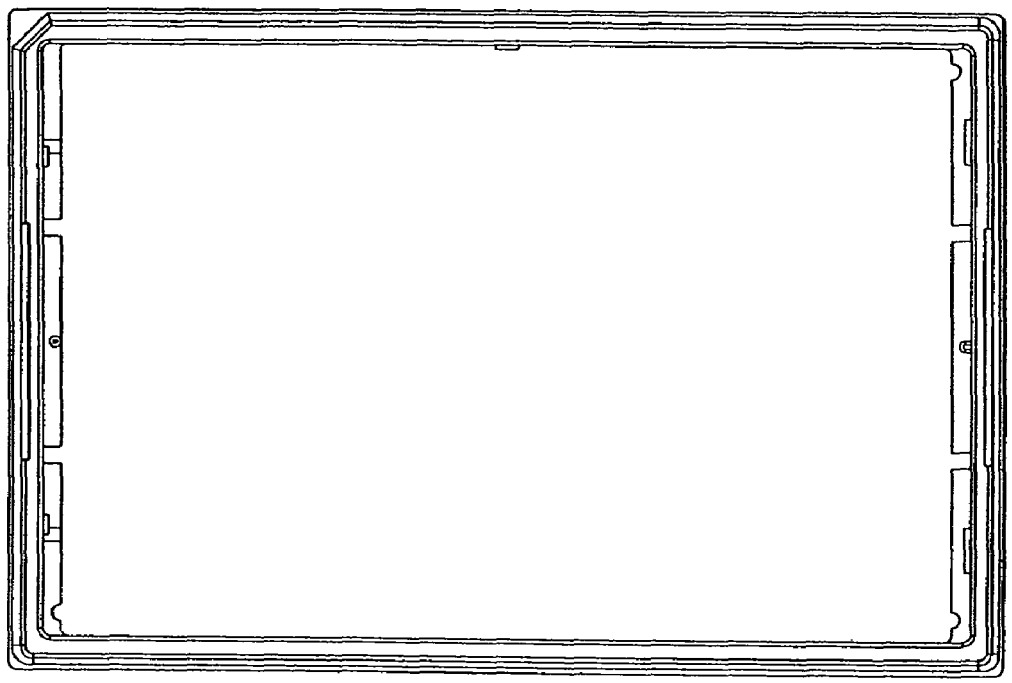
Figure 110:
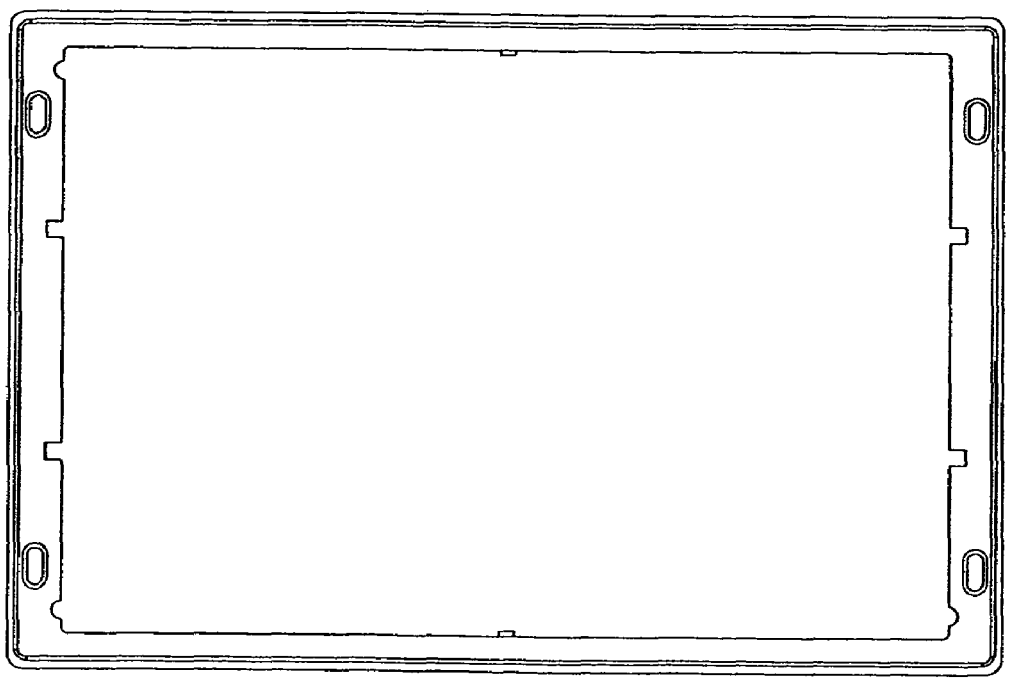
Figure 111:
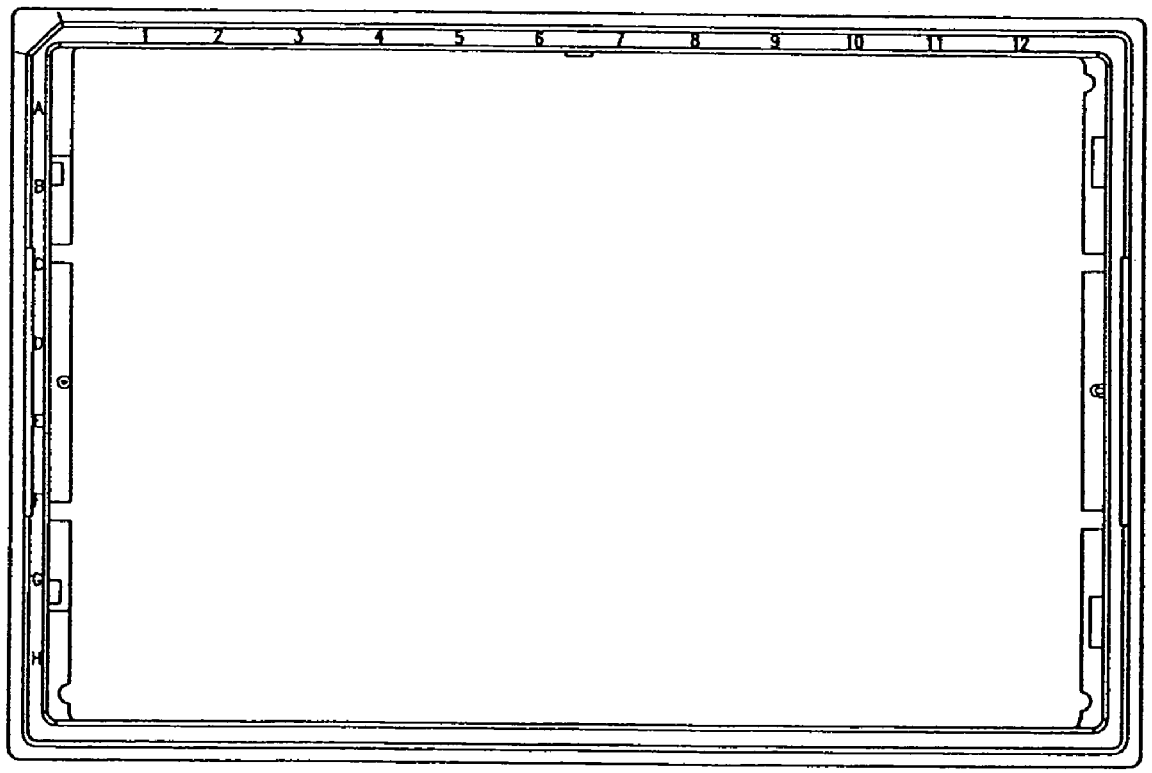
Figure 112:
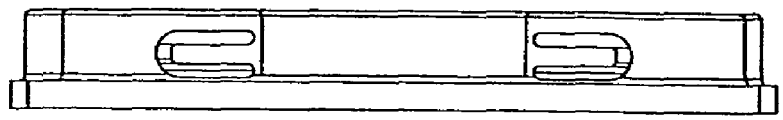
Figure 113:
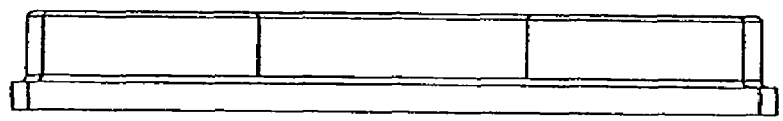
Figure 114:
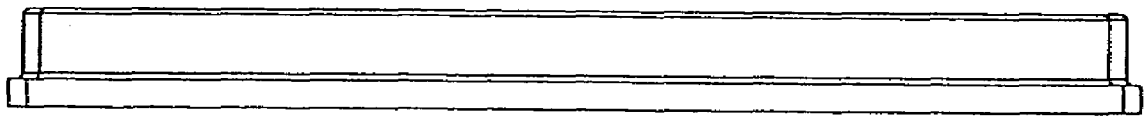
Figure 115:
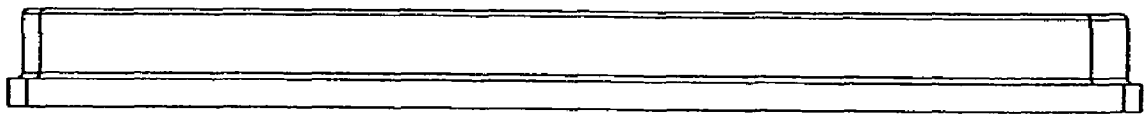
Figure 116:
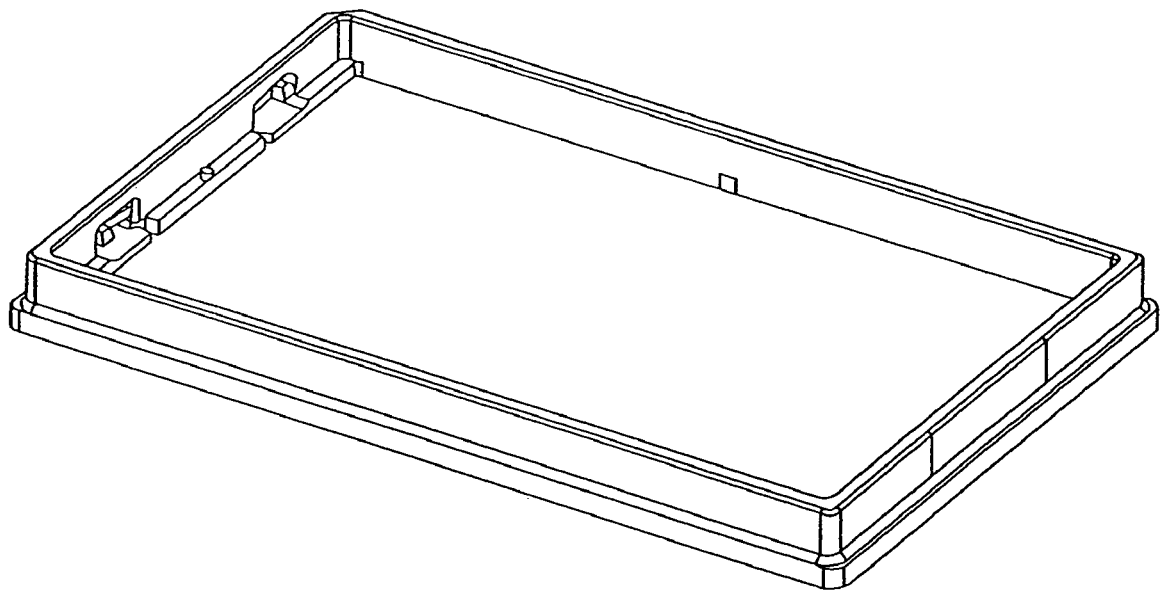
Figure 117:
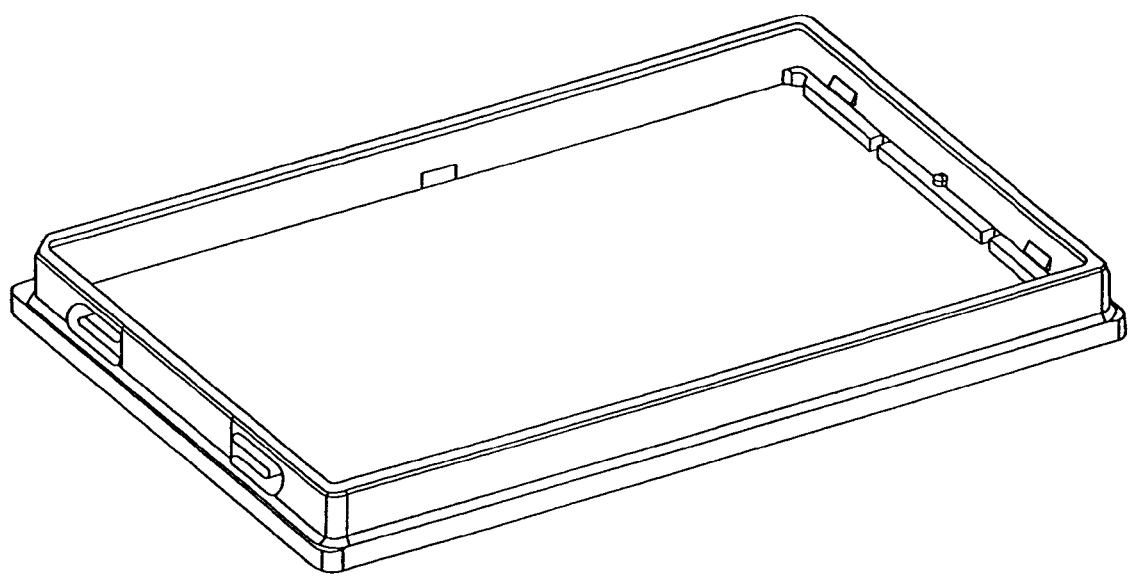
Figure 118:
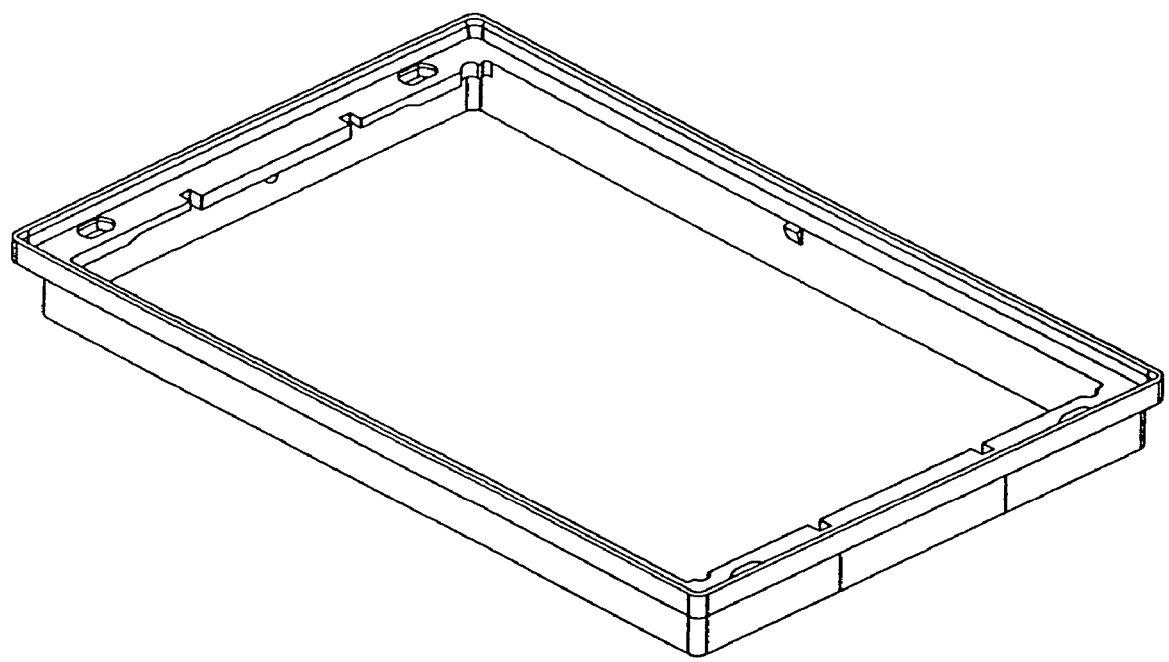

FIG. 109: is a top plan view of a caddy for a multi-well platform,
FIG. 110: is a bottom plan view thereof,
FIG. 111: is a top plan view thereof with additional surface ornamentation,
FIG. 112: is a left elevation view thereof,
FIG. 113: is a right elevation view thereof,
FIG. 114: is a front elevation view thereof,
FIG. 115: is a back elevation view thereof,
FIG. 116: is a top, front, and right perspective view thereof,
FIG. 117: is a top, front, and left perspective view thereof, and
FIG. 118: is a bottom, front, and right perspective view thereof.

Q. Combination of a Multi Well Platform and Caddy

Figure 119:
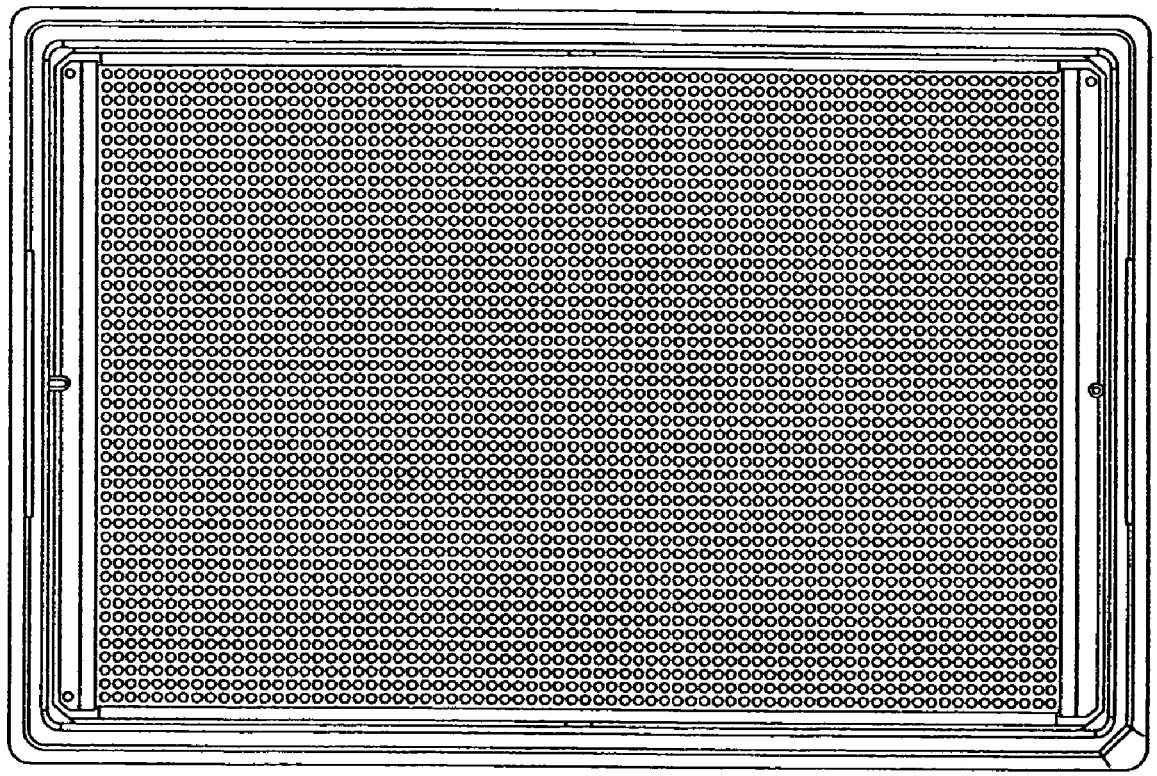
Figure 120:
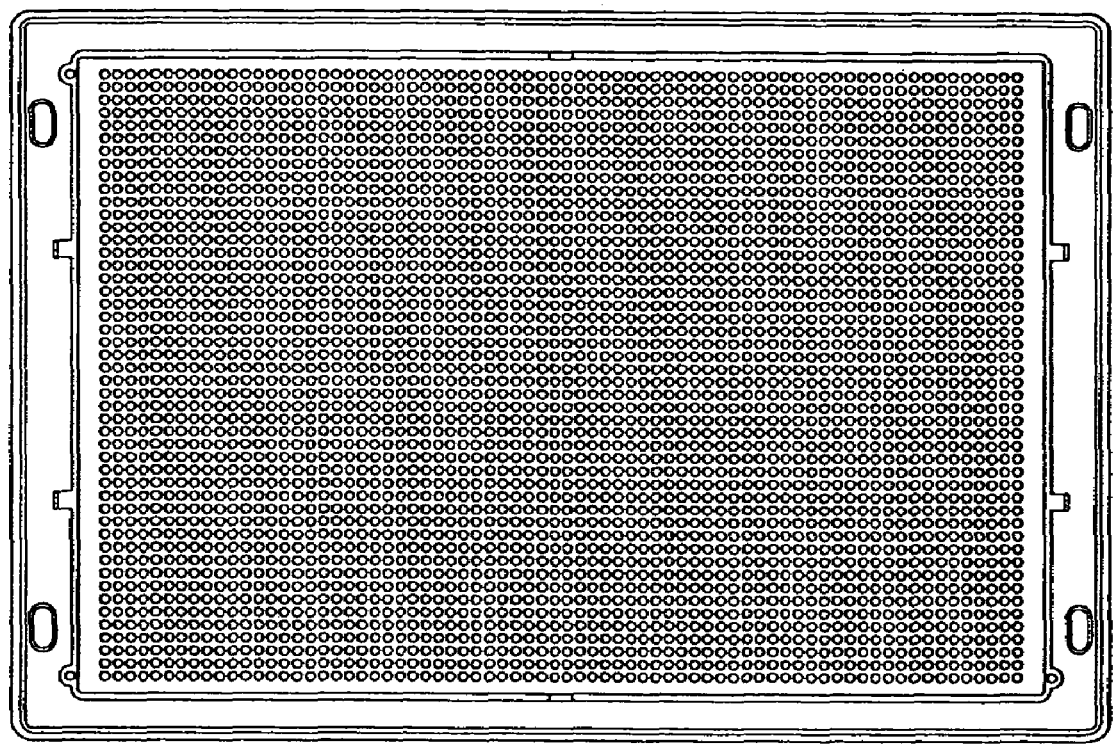
Figure 121:
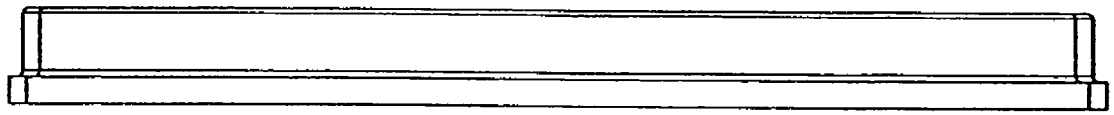
Figure 122:
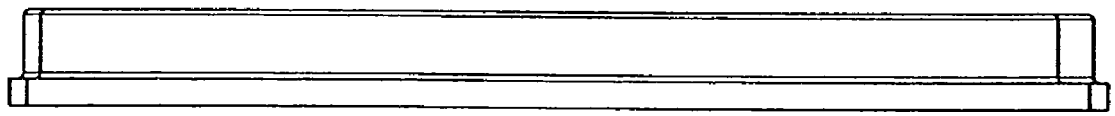
Figure 123:
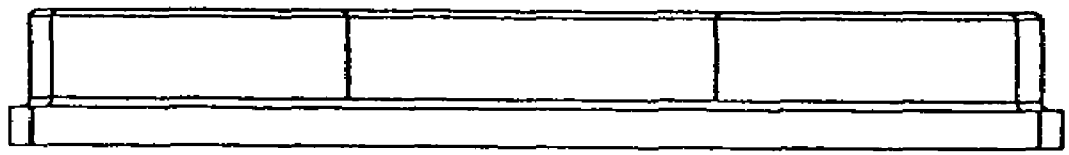
Figure 124:
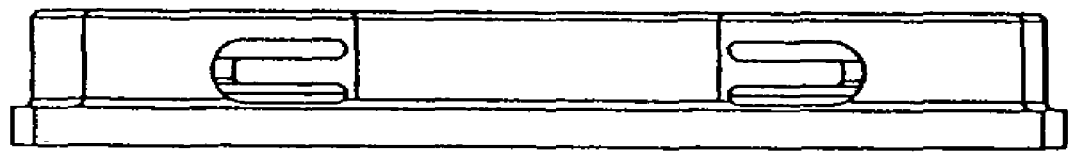
Figure 125:
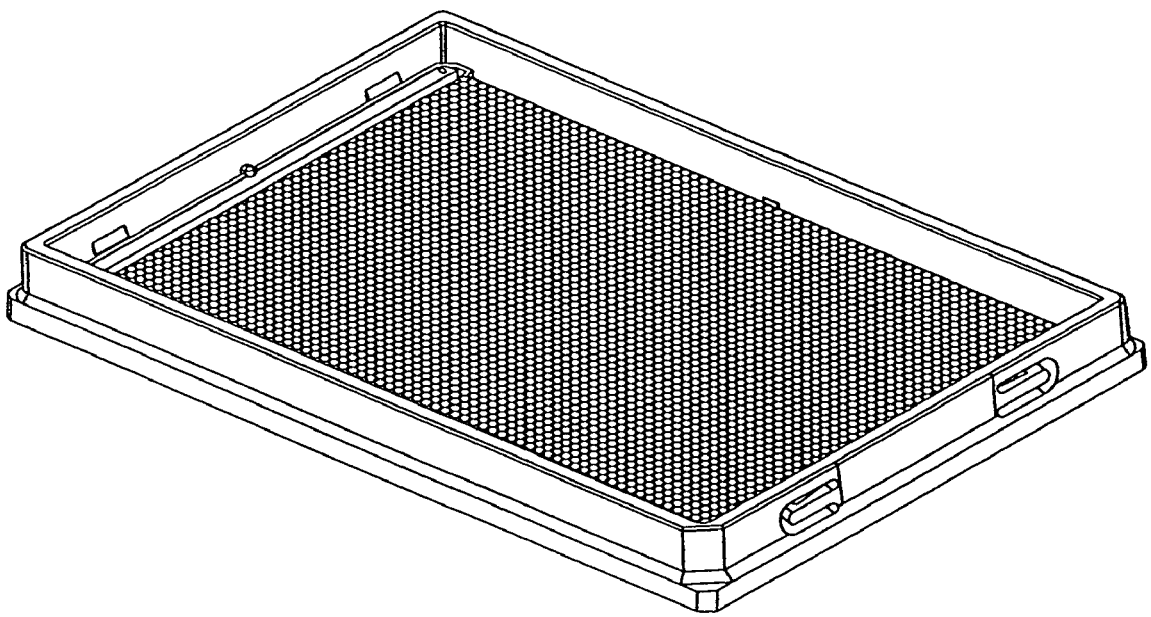
Figure 126:
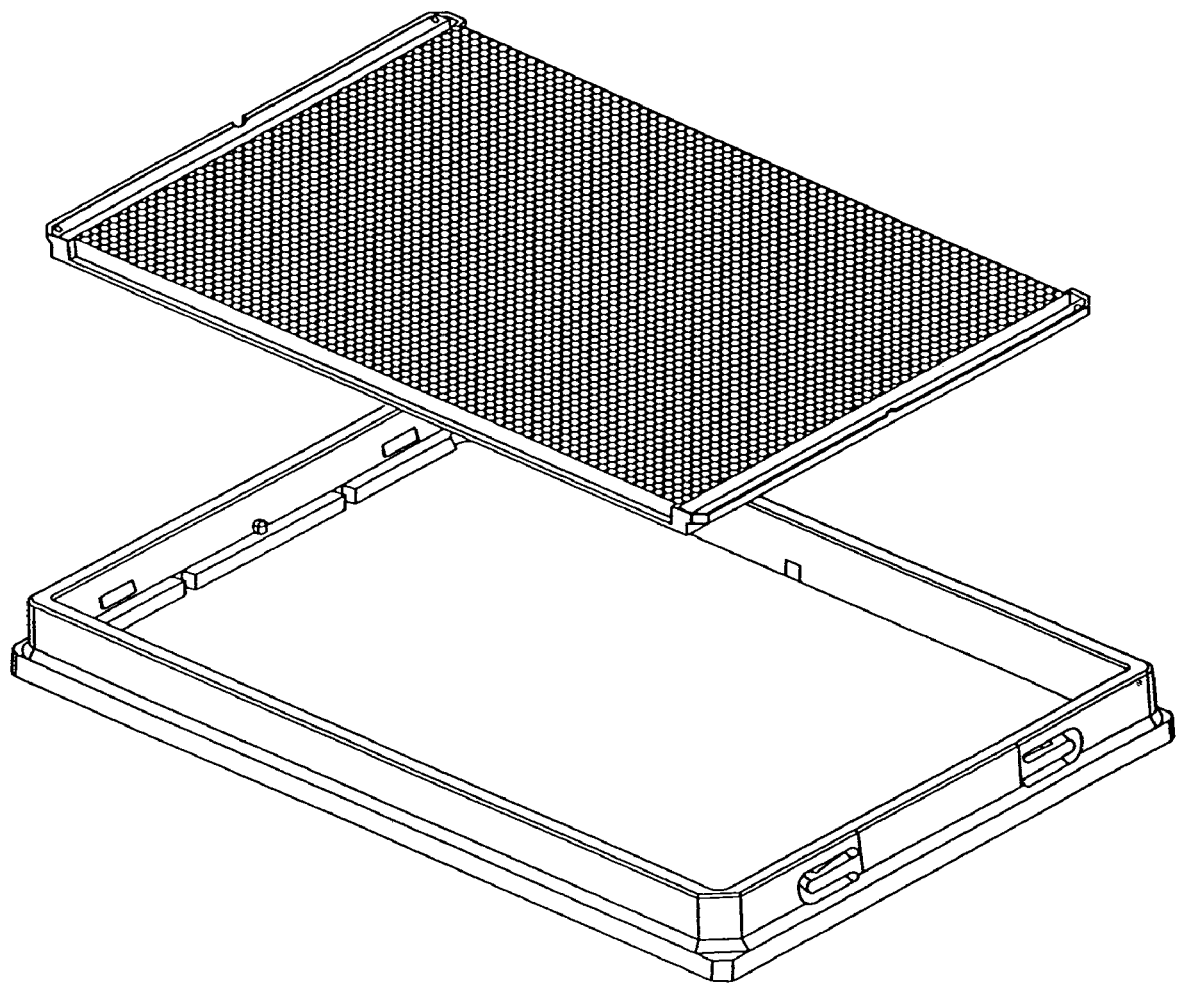

FIG. 119: is a top plan view of a combination of a multi-well platform and caddy,
FIG. 120: is a bottom plan view thereof,
FIG. 121: is a left elevation view thereof,
FIG. 122: is a right elevation view thereof,
FIG. 123: is a front elevation view thereof,
FIG. 124: is a back elevation view thereof,
FIG. 125: is a top, front, and right perspective view thereof, and
FIG. 126: is an exploded view thereof

R. Combination of a Multi Well Platform, Caddy and Lid

Figure 127:
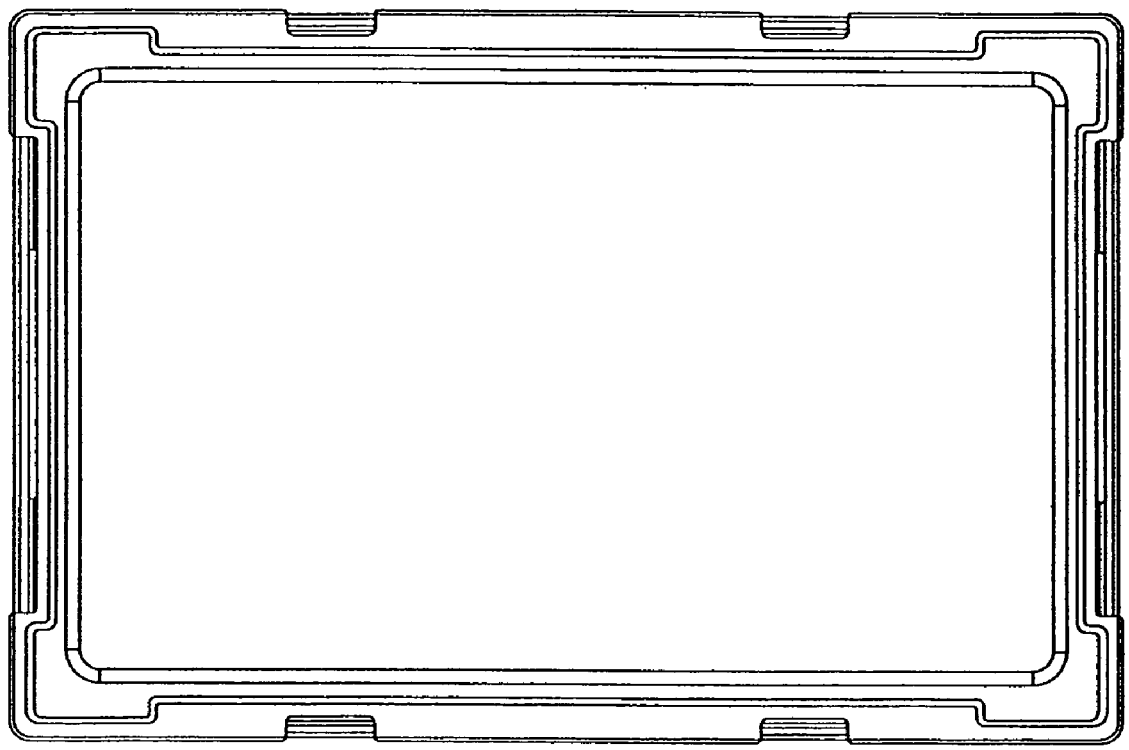
Figure 128:
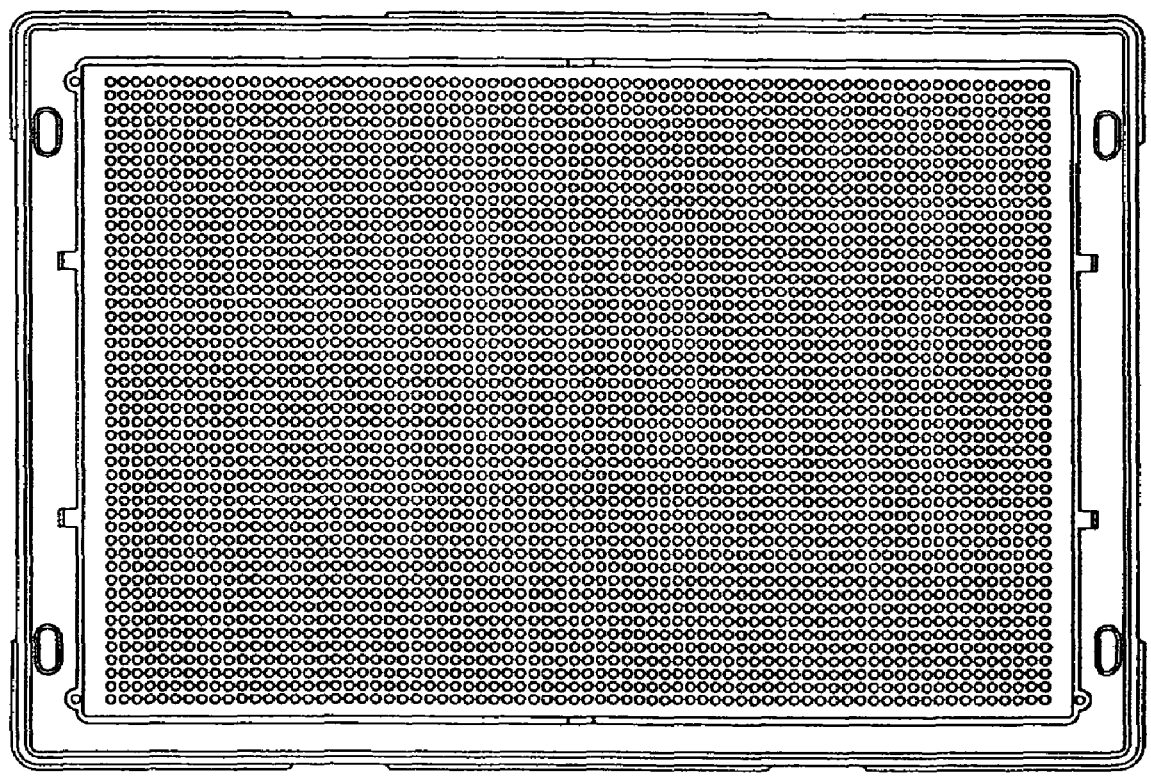
Figure 129:
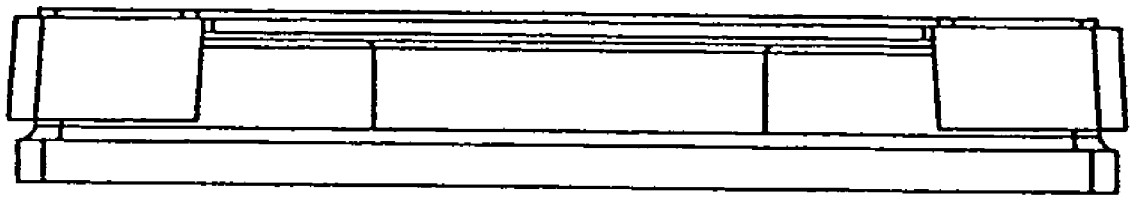
Figure 130:
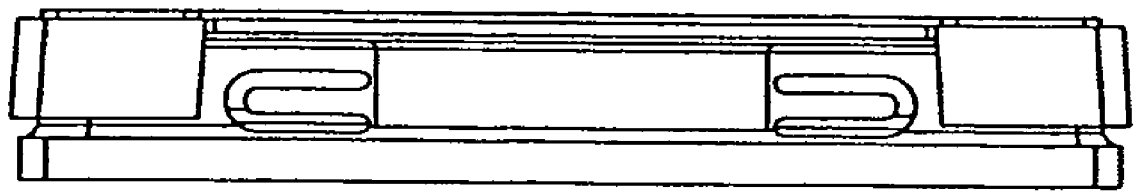
Figure 131:
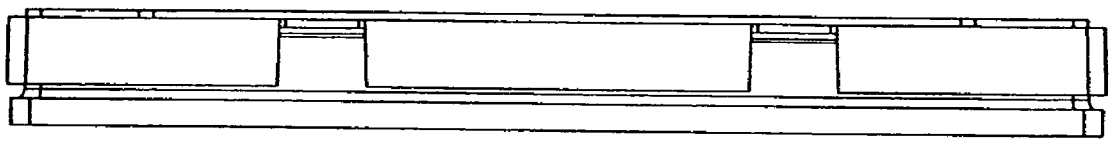
Figure 132:
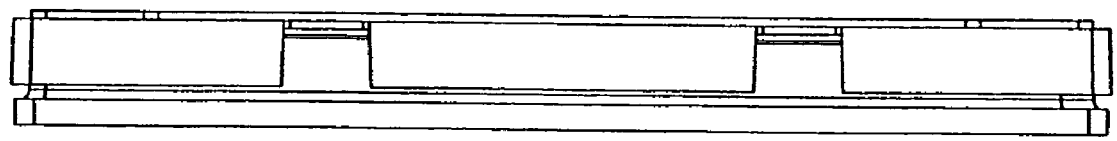
Figure 133:
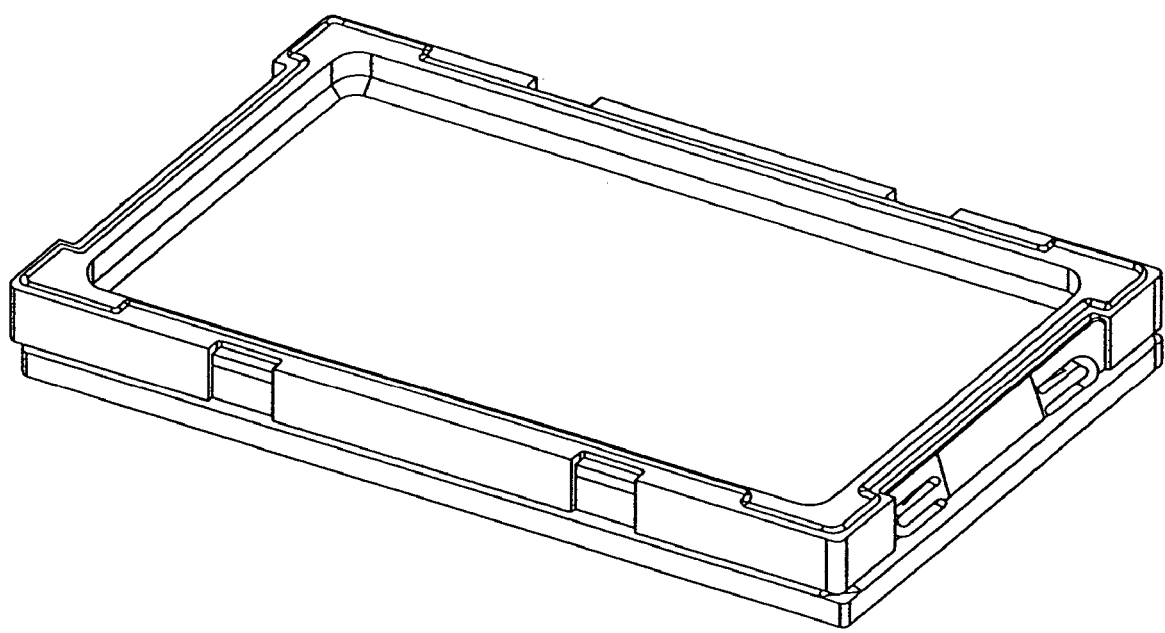
Figure 134:
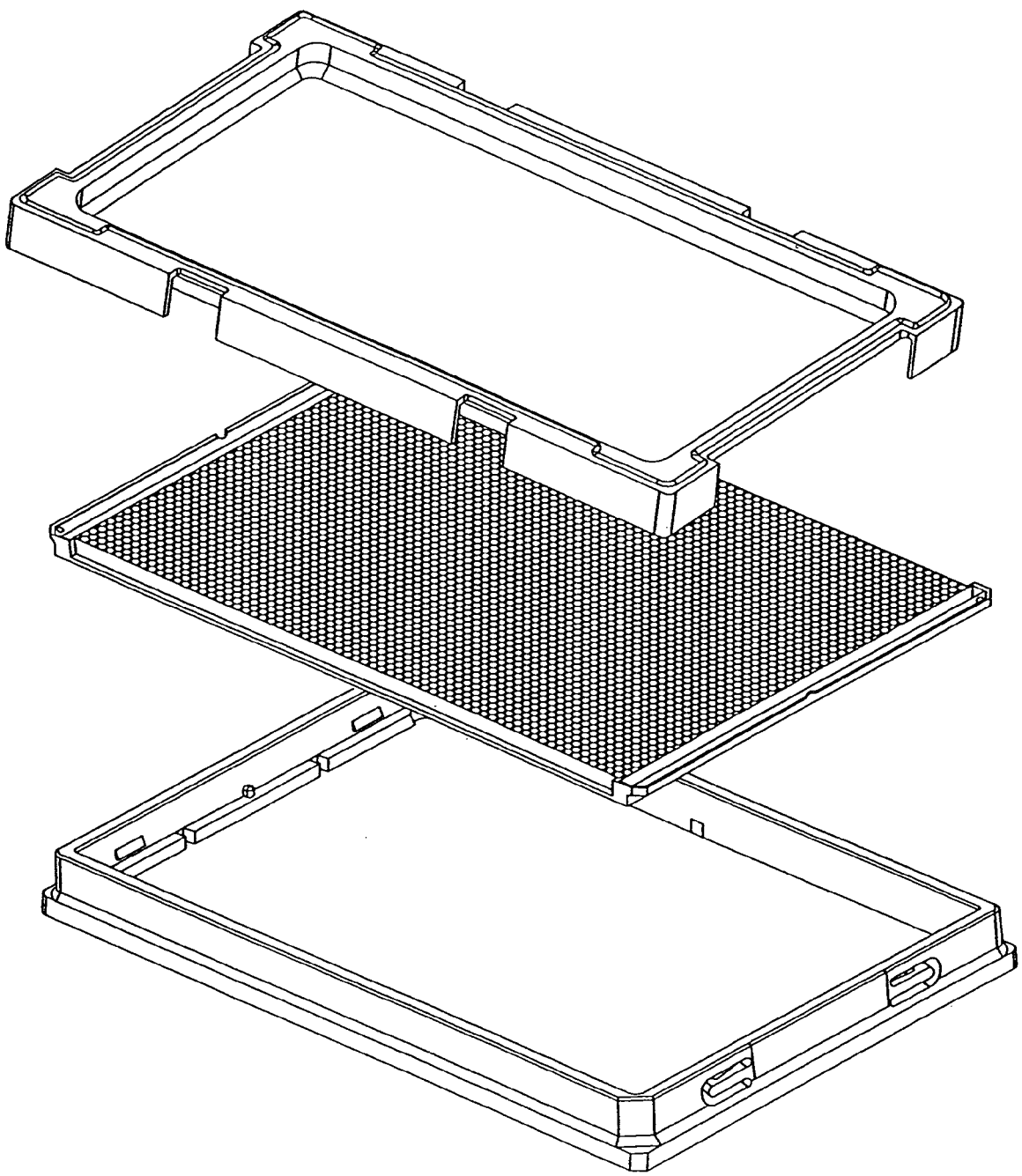

FIG. 127: is a top plan view of a combination of a multi-well platform, caddy and lid,
FIG. 128: is a bottom plan view thereof,
FIG. 129: is a left elevation view thereof,
FIG. 130: is a right elevation view thereof,
FIG. 131: is a front elevation view thereof,
FIG. 132: is a back elevation view thereof,
FIG. 133: is a top, front, and right perspective view thereof,
FIG. 134: is an exploded view thereof, and
FIG. 135A and 135B: depict a cross-section of two embodiments of a multi-well platform.

We claim:

1. A combination, comprising:
    a multi-well platform having a plurality of wells, the bottom of each well being a polycycloolefin material;
    a caddy having a cavity to receive the multi-well platform, the cavity being shaped such that the plurality of wells are not obscured by the caddy when viewed from the bottom; and
    a lid, the lid being dimensioned to cover at least the plurality of wells.

2. The combination of claim 1, wherein the multi-well platform has a footprint and the cavity is adapted to receive the footprint.

3. The combination of claim 2, wherein the footprint is approximately that of a standard 96-well microtiter plate.

4. The combination of claim 1, wherein the caddy has a footprint approximately that of a standard 96-well microtiter plate.

5. The combination of claim 1, wherein the caddy has ornamentation.

6. The combination of claim 5, wherein the ornamentation includes one or more pins, grooves, flanges and/or indentations.

7. The combination of claim 1, wherein the multi-well platform and the caddy both have a footprint approximately that of a standard 96-well microtiter plate.

8. The multi-well platform of claim 1, wherein the number of wells can be between 50 and 10000.

9. The combination of claim 1, wherein the lid further covers the caddy.

10. A multi well platform, comprising:
    a well field having a plurality of wells, the bottom of each well being a polycycloolefin material;
    a border; and
    a lid, the lid being dimensioned to cover at least the plurality of wells;
    wherein the polycycloolefin material has high transmittance and low fluorescence.

11. The multi well platform of claim 10, wherein the number of wells can be between 50 and 10000.

12. A multi well platform, comprising:
    a) a well field having a bottom comprising a polycycloolefin material;
    b) a border; and
    c) a lid, the lid being dimensioned to cover at least the well fields;
    wherein the polycycloolefin material has high transmittance and low fluorescence.

13. The multi well platform of claim 12, wherein the well field includes a plurality of wells.

14. The multi well platform of claim 13, wherein the bottom of each well is the polycycloolefin material.

15. The multi-well platform of claim 13, wherein the number of wells is between 50 and 10000.

16. The multi well platform of claim 12, wherein the lid further covers the border.

17. The multi well platform of claim 12, wherein the lid is opaque.

18. The multi well platform of claim 12, wherein the lid is pigmented.

19. The multi well platform of claim 1, wherein the fluorescence of the polycycloolefin material is not more than 200% higher than the fluorescence of glass having thickness between about 85 μm to 130 μm at excitation wavelengths between about 300 nm and 400 nm and at emission wavelengths between about 350 nm and 800 nm.

20. The multi well platform of claim 1, wherein the fluorescence of the polycycloolefin material is not more than 100% higher than the fluorescence of glass having thickness between about 85 μm to 130 μm at excitation wavelengths between about 300 nm and 400 nm and at emission wavelengths between about 350 nm and 800 nm.

* * * * *